US005795759A

United States Patent [19]
Rosazza et al.

[11] Patent Number: 5,795,759
[45] Date of Patent: Aug. 18, 1998

[54] CARBOXYLIC ACID REDUCTASE, AND METHODS OF USING SAME

[75] Inventors: John P. N. Rosazza; Tao Li, both of Iowa City, Iowa

[73] Assignee: The University of Iowa Research Foundation, Iowa City, Iowa

[21] Appl. No.: 813,437

[22] Filed: Mar. 10, 1997

[51] Int. Cl.$^6$ .................................. C12P 7/24; C12N 9/02
[52] U.S. Cl. ............................................. 435/189; 435/147
[58] Field of Search ................................... 435/147, 189; 426/44

[56] References Cited

U.S. PATENT DOCUMENTS

| | | | |
|---|---|---|---|
| 5,017,388 | 5/1991 | Rabenhorst et al. | 426/44 |
| 5,057,424 | 10/1991 | Knuth et al. | 435/240.48 |
| 5,128,253 | 7/1992 | Labuda et al. | 435/147 |
| 5,262,315 | 11/1993 | Gross et al. | 435/147 |
| 5,279,950 | 1/1994 | Labuda et al. | 435/147 |

OTHER PUBLICATIONS

Arfmann et al., "Microbial reduction of aromatic carboxylic acids," *Z. Naturforsch* 48c:52–57 (1993).

Bachman et al., "Reduction of salicylate to saligenin by *Neurospora*," *Arch. Biochem. Biophys.* 91:326 (1960).

Chen and Rosazza, "Microbial transformation of ibuprofen by a *Nocardia* species," *Appl. Environ. Microbiol.* 60(4):1292–1296 (1994).

Clonis et al., "The interaction of yeast hexokinase with Procion Green H–4G," *Biochem. J.* 197:203–211 (1981).

Clonis, "Dye–ligand chromatography." p. 33. in *Reactive Dyes in Protein and Enzyme Technology.* 1989. Clonis, Atkinson, Bruton, and Lowe (ed.), Stockton Press, New York, N.Y.

Glazer, "The specific binding of Biebrich Scarlet to the active site of α-chymotrypsin," *J. Biol. Chem.* 242(19):4528–4533 (1967).

Gross et al., "Reduktion aromatischer Säuren zu Aldehyden und Alkoholen im zellfreien System. 1. Reiningung und Eigenschaften von Aryl–Aldehyd: NADPOxidoreduktase aus *Neurospora crassa*," *Eur. J. Biochem.* 8:413–419; 420–425 (1969).

Gross, "Formation and reduction of intermediate acyl–adenylate by aryl–aldehyd NADP oxidoreductase from *Neurospora crassa*," *Eur. J. Biochem.* 31:585–592 (1972).

Gurujeyalakshmi et al., "Dissimilation of ferulic acid by *Bacillus subtilis*," *Current Microbiol.* 16:69–73 (1987).

Hagedorn et al., "Microbial biocatalysis in the generation of flavor and fragrance chemicals," *Ann. Rev. Microbiol.* 48:773–800 (1994).

Hempel et al., "Aldehyde dehydrogenases: widespread structural and diversity within a shared framework." *Protein Sci.* 2:1890–1900 (1993).

Huang, et al., "Mechanisms of ferulic acid conversions to vanillic acid and guaiacol by *Rhodotorula rubra*," *J. Biol. Chem.* 268:23954–23958 (1993).

Hughes et al., "Metal ion–promoted binding of proteins to immobilized triazine dye affinity adsorbents," *Biochim. Biophys. Acta* 700:90–100 (1982).

Ishikawa et al., "The degradation by *Polyporus versicolor* and *Formes fomentarius* of aromatic compounds structurally related to softwood lignin," *Archiv. Biochem. Biophys.* 100:140–149 (1963).

Jezo & Zemek, "Enzymatische reducktion einiger aromatischer Carboxys.," *Chem. Papers* 40(2):279–281 (1986).

Jurkov et al., "Biodegradation of aromatic carboxylic acids by *Pseudomonas mira*," *FEMS Microbiol. Lett.* 111:245–250 (1993).

Kato et al., "Microbiol reduction of benzoate to benzym alcohol," *Agric. Biol. Chem.* 52(7):1885–1886 (1988).

Kato et al., "Purification and characterization of aromatic acid reductase from *Nocardia asteroides* JCM 3016," *Agric. Biol. Chem.* 55(3):757 (1991).

McArdell et al., "The isolation of a peptide from the catalytic domain of *Bacillus stearothermophilus* tryptophy–tRNA synthetase," *Biochem. J.* 243:701–707 (1987).

McArdell et al., "Probing the substrate–binding sites of aminoacyl–tRNA synthetase with Procion dye Green HE–4BD," *Biochem. J.* 258:714–721 (1989).

Prince et al., "Just plain vailla?" *Trends Biol. Sci.* 19:521 (1994).

Raman et al., "Metabolism of some aromatic acids by *Aspergillus niger*," *J. Bacteriol.* 84:1340–1341 (1962).

Riendeau et al., "Evidence for a fatty acid reductase catalyzing the synthesis of aldehydes for the bacterial bioluminescent reaction," *J. Biol. Chem.* 254(16):7488–7490 (1979).

Rodriquez et al., "Fatty acyl–AMP as an intermediate in fatty acid reduction to aldehyde in luminescent bacteria," *J. Biol. Chem.* 260(2):771–774 (1985).

Rosazza et al., "Biocatalytic transformation of ferulic acid: an abundant aromatic natural product," *J. Ind. Microbiol.* 15:457–471 (1995).

Small et al., "Affinity labeling of enzymeswith triazine dyes," *Eur. J. Biochem.* 128:119–123 (1982).

(List continued on next page.)

Primary Examiner—Robert A. Wax
Assistant Examiner—Einar Stole
Attorney, Agent, or Firm—Zarley, McKee, Thomte, Voorhees, & Sease

[57] ABSTRACT

The present invention is directed to a novel, biologically-derived carboxylic acid reductase, also referred to herein as an aryl-aldehyde oxidoreductase, that has been isolated and purified from Nocardia sp. strain NRRL 5646, and to methods of using the carboxylic acid reductase as a biocatalyst for the reduction of carboxylic acids or their derivatives to the corresponding useful product(s). In a preferred embodiment, the invention is directed to biochemically-produced vanillin, and to the methods of its production by the biocatalytic reduction of vanillic acid, or a precursor or derivative thereof, in a reaction comprising the substantially purified, biologically-derived carboxylic acid reductase.

5 Claims, 6 Drawing Sheets

OTHER PUBLICATIONS

Sutherland et al., "Metabolism of cinnamic, p-coumaric, and ferulic acids by *Streptomyces setonii*," *Can. J. Microbiol.* 29:1253–1257 (1983).

Toms et al., "The degradation of trans-ferulic acid by *Pseudomonas acidovorans*," *Biochemistry* 9:337–343 (1970).

Tsuda et al., "Asymmetric reduction of 2-methyl-2-aryloxyacetic acids by *Glomerella cingulata*," *Agric. Biol. Chem.* 48(5):1373–1374 (1984).

Tsuda et al., "Microbial reduction of 2-phenylpropionic acid 2-benzyloxypropionic acid and 2-(2-furfuryl)propionic acid," *Chem. Pharm. Bull.* 33(11):4657–4661 (1985).

White et al., "Carboxylic acid reductase: a new tungsten enzyme catalyzes the reduction of non-activated carboxylic acids to aldehydes," *Eur. J. Biochem.* 184:89–96 (1989).

Saeki et al. (1994) Cloning and characterization of a Nocardia corallina B-276 gene cluster encoding alkene monooxygenase. Journal of Fermentation and Bioengineering 78 (6): 399–406, Jun. 1994.

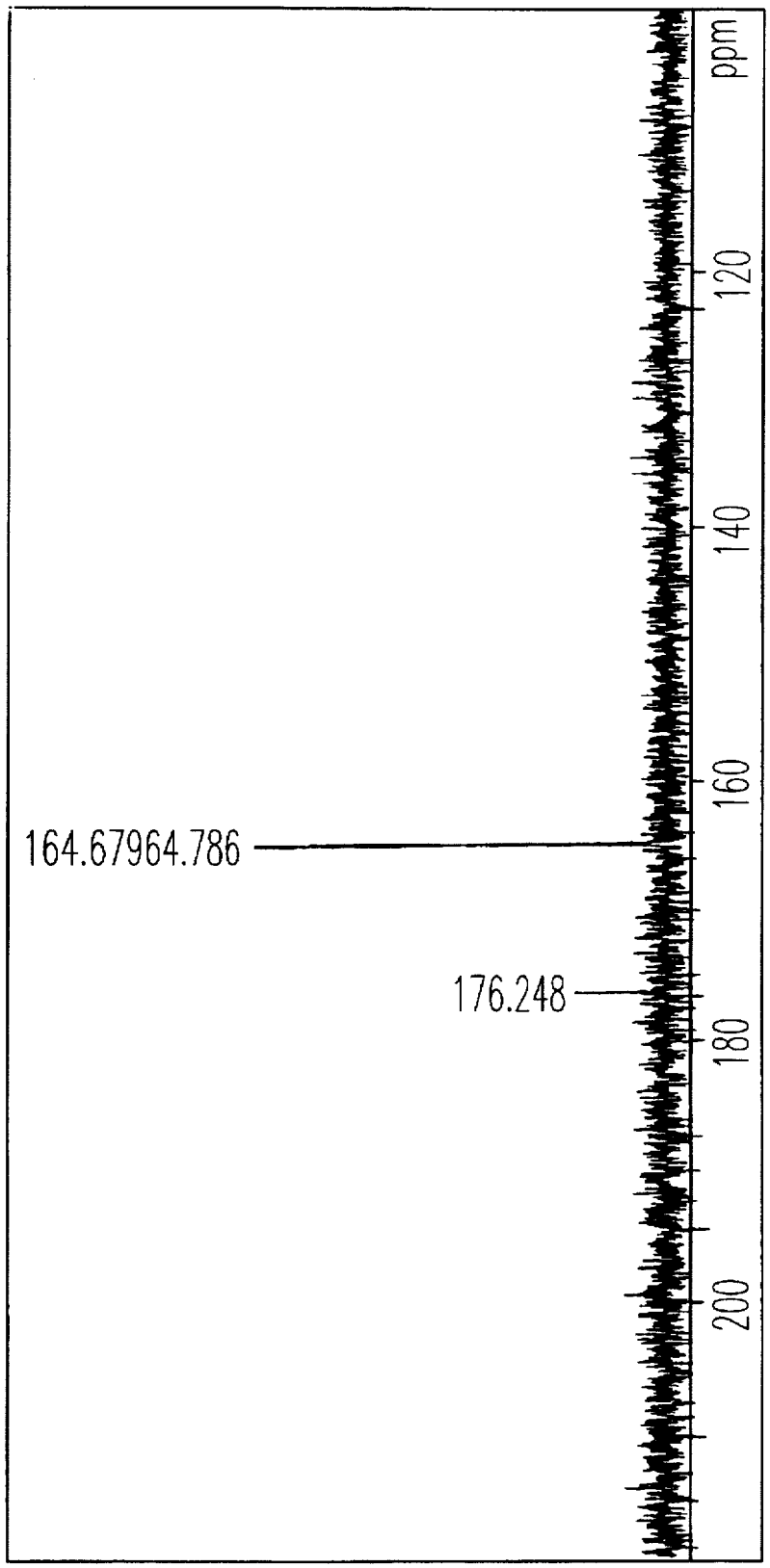

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( i i ) MOLECULE TYPE: peptide ( v ) FRAGMENT TYPE: N-terminal ( x i ) SEQUENCE DESCRIPTION: SEQ ID NO:1:

```
Ala Val Asp Ser Pro Asp Glu Arg Leu Gln Arg Arg Ile Ala Xaa Leu
 1               5                  10                  15
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: Not Relevant ( i i ) MOLECULE TYPE: peptide ( v ) FRAGMENT TYPE: internal ( x i ) SEQUENCE DESCRIPTION: SEQ ID NO:2:

```
Lys Leu Ser Gln Gly Glu Phe Val Ala His Leu Xaa Ala Val
 1               5                  10
```

CARBOXYLIC ACID REDUCTASE, AND METHODS OF USING SAME

Statement of Government Rights in the Invention

Part of the work performed during the development of this invention was supported by the U.S. Department of Agriculture through the Byproducts for Biotechnology Consortium. Thus, the U.S. Government may have certain rights in this invention.

BACKGROUND OF THE INVENTION

1. Field of the Invention

The present invention is directed to a purified, biologically-derived carboxylic acid reductase, and to methods of using the carboxylic acid reductase as a biocatalyst for the reduction of carboxylic acids or their derivatives to their corresponding useful product(s).

2. Description of Related Art

Microorganism-produced enzymes are widely used as a class of biocatalytic reagents in synthetic organic chemistry in a wide variety of reactions including, e.g., oxidations, reductions, hydrolyses, and carbon-carbon bond ligations. Enzyme reactions, such as those catalyzed by esterases, for example, may be used either hydrolytically or to synthesize esters, depending on whether the reaction medium is aqueous or organic in composition.

Biocatalysts are valued for their intrinsic abilities to bind organic substrates and to catalyze highly specific and selective reactions under the mildest of reaction conditions. These selectivities and specificities are realized because of highly rigid interactions occurring between the enzyme active site and the substrate molecule. Biocatalytic reactions are particularly useful when they may be used to overcome difficulties encountered in catalysis achieved by the use of traditional chemical approaches.

The reduction of carboxylic acids by microorganisms is a relatively new biocatalytic reaction that has not yet been widely examined or exploited. Jezo and Zemek reported the reduction of aromatic acids to their corresponding benzaldehyde derivatives by Actinomycetes in Chem. Papers 40(2):279–281 (1986). Kato et al. reported the reduction of benzoate to benzyl alcohol by Nocardia asteroides JCM 3016 (Agric. Biol. Chem. 52(7):1885–1886 (1988)), and Tsuda et al. described the reduction of 2-aryloxyacetic acids (Agric. Biol Chem. 48(5):1373–1374 (1984)) and arylpropionates (Chem. Pharm. Bull. 33(11):4657–4661 (1985)) by species of Glomerella and Gloeosporium. Microbial reductions of aromatic carboxylic acids, typically to their corresponding alcohols, have also been observed with whole cell biotransformations by Clostridium thermoaceticum (White et al., Eur. J. Biochem. 184:89–96 (1989)), and by Neurospora (Bachman et al., Arch. Biochem. Biophys. 91:326 (1960)). More recently, carboxylic acid reduction reactions have reportedly been catalyzed by whole cell preparations of Aspergillus niger, Corynespora melonis and Coriolus (Arfmann et al., Z. Naturforsch 48c:52–57 (1993); cf., Raman et al., J. Bacteriol. 84:1340–1341 (1962)), and by Nocardia (Chen and Rosazza, Appl. Environ. Microbiol. 60(4):1292–1296 (1994)).

Carboxylic acid reductases are complex, multicomponent enzyme systems, requiring the initial activation of carboxylic acids via formation of AMP and often coenzyme A intermediates (see, e.g., Hempel et al., Protein Sci. 2:1890–1900 (1993). However, an enzymatic reaction offers significant advantages over existing methods used in chemical reductions of carboxylic acids, or their derivatives. Unlike many substrates subjected to biocatalytic reactions, carboxylic acids are generally water soluble, rendering them of potentially broad application to this class of enzyme. The carboxylic acid reduction reaction appears to bear the usual desirable features of functional group specificity. It also functions well under mild reaction conditions and produces a high yield of product. The reduction of the activated carboxylic acid intermediate occurs step-wise to give aldehyde, and then alcohol products (Gross et al., Eur. J. Biochem. 8:413–419; 420–425 (1969); Gross, Eur. J Biochem. 31:585–592 (1972)).

In the present inventor's laboratory, whole cell preparations of Nocardia sp. NRRL 5646 were found to be highly enantioselective in the reduction of isomeric ibuprofen substrates (Appl. Environ. Microbiol. 60(4):1292 (1994)). However, with this organism, the substrate specificity for carboxylic acids was significantly different than that which had been reported by Kato et al for Nocardia asteroides in Agric. Biol. Chem. 52(7):1885 (1988), and by others. Consequently, recognizing the importance of identifying and understanding the biocatalytic enzyme capable of reducing a carboxylic acid to its aldehyde product, the inventors developed a method of rapid purification and characterization of the enzyme, and of determining its enantioselectivity and effect on a series of aryl-carboxylic acid substrates. The purified enzyme of the present invention was classified as an aryl-aldehyde oxidoreductase, also correctly denominated a carboxylic acid reductase (EC 1.2.1.30).

It will be appreciated that the availability of large quantities of the novel reductase made possible by the present invention, permits an crucial examination of the structure of the enzyme and an understanding of the mechanisms involved in the catalysis. In the case of many aldehydes, there has been a long-felt need to locate commercially viable methods for their production from plentiful, low-cost starting materials.

Vanillin is a classic example of such a product. Natural vanilla, one of the most important flavors used in the food industry, is presently extracted from the cured pods of the flowers of Vanilla planifolia. Yet because of the escalating cost of producing natural vanilla, methods are constantly being sought to manufacture vanillin (3-methoxy-4-hydroxybenzaldehyde), the most important organoleptic component in vanilla. Over 12,000 tons of vanillin are currently produced annually from byproducts of the petrochemical and wood pulping industries (Prince et al., Trends. Biol. Sci. 19:521(1994); Hagedorn et al., Ann. Rev. Microbiol 48:773–800 (1994)). Nevertheless, the demand for natural and environmentally friendly products have spawned efforts to produce vanillin biochemically by microbial transformation from natural substrates including phenolic stibenes (Japanese Patent No. 2,195,871), eugenol (U.S. Pat. No. 5,017,388; Japanese Patent No. 5,227,980), and ferulic acid and benzenoid precursors (U.S. Pat. Nos. 5,262,315 and 5,128,253). However, despite the continuing effort to develop microbial transformations for vanillin production, the yields provided by the published methods are low, and the time for transformation is long.

In response to this need, the present invention provides not only a greater understanding of the metabolic pathways, cofactors and the enzymes needed to improve the yield of such valuable aldehyde and alcohol products by manipulating the metabolic network, but it also discloses for the first time, a safe and efficient method of producing GRAS vanillin from an inexpensive and abundant source, vanillic acid and its precursors, by a microbiologically-derived, purified, aryl-aldehyde oxidoreductase (carboxylic acid reductase). Moreover, further advancement of the art will be greatly enhanced by the inventors' purification of the enzyme, and the present invention will provide many new ways to study the mechanisms involved in biocatalysis.

SUMMARY OF THE INVENTION

The present invention concerns a novel, biologically-derived carboxylic acid reductase, also referred to herein as an aryl-aldehyde oxidoreductase, that has been isolated and substantially purified from Nocardia sp. strain NRRL 5646, and to methods of using same.

It is an object of the present invention to provide a substantially purified, biologically-derived carboxylic acid reductase, or aryl-aldehyde oxidoreductase, wherein the enzyme is characterized by its ability to biocatalytically reduce a carboxylic acid, or a derivative thereof, to the corresponding product(s). It is, moreover, an object of the invention to provide the carboxylic acid reductase from Nocardia sp., as exemplified by that which is isolated from Nocardia sp. strain NRRL 5646.

It is a further object of the present invention to provide a method of biocatalytically reducing a carboxylic acid, or a derivative thereof, to its corresponding product(s), comprising using a substantially purified, biologically-derived carboxylic acid reductase, as exemplified by that which is isolated from Nocardia sp. strain NRRL 5646. It is also an object of the invention to provide a method of biocatalytically reducing a carboxylic acid, or a derivative thereof, to its corresponding product(s), comprising the steps of: a) mixing an effective amount of the substantially purified, biologically-derived carboxylic acid reductase with the carboxylic acid, or its derivative, to activate reduction; b) incubating the mixture for a period of time to achieve reduction of the carboxylic acid, or its derivative into the corresponding product(s); and c) extracting the product(s).

It is a particular object of the invention to provide the method of biocatalytically reducing a carboxylic acid, or a derivative thereof, to its corresponding aldehyde product(s). In addition, it is an object to provide the aldehyde product(s) produced by the biocatalytic action of the substantially purified carboxylic acid reductase of the present invention on a carboxylic acid starting material, or on a derivative thereof.

It is also a particular object of the invention to provide the method of biocatalytically reducing a carboxylic acid, or a derivative thereof, to its corresponding intermediary by-product(s), as exemplified by acyl-AMP analogs.

It is another object of the present invention to provide a method of biocatalytically reducing vanillic acid, or a precursor or derivative thereof, to vanillin, comprising using a substantially purified, biologically-derived carboxylic acid reductase, as exemplified by that which is isolated from Nocardia sp. strain NRRL 5646. It is also an object of the invention to provide a method of biocatalytically reducing vanillic acid, or a precursor or derivative thereof, to vanillin, comprising the steps of: a) mixing an effective amount of the substantially purified, biologically-derived carboxylic acid reductase with the vanillic acid or, a precursor or derivative thereof, to activate reduction; b) incubating the mixture for a period of time to achieve reduction of the vanillic acid, or its precursor or derivative into the vanillin; and c) extracting the vanillin product.

In addition, it is an object of the present invention to provide vanillin produced by microbiological methods, including that which is produced by the biocatalytic action of the substantially purified carboxylic acid reductase of the present invention on vanillic acid, or on a precursor or derivative thereof Additional objects, advantages and novel features of the invention will be set forth in part in the description which follows, and in part will become apparent to those skilled in the art on examination of the following, or may be learned by practice of the invention.

BRIEF DESCRIPTION OF THE DRAWINGS

FIG. 7 depicts the microbial and enzymatic transformation pathways for vanillic acid and o-benzyl vanillic acid by Nocardia sp NRRL 5646.

DESCRIPTION OF THE PREFERRED EMBODIMENTS

Figure 1:
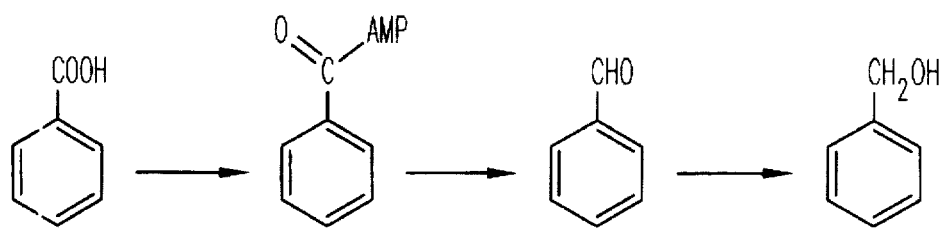
FIG. 1 depicts the pathway for benzoic acid reduction by Nocardia sp. NRRL 5646.

The present invention is directed to a novel, biologically-derived carboxylic acid reductase, also referred to herein as an aryl-aldehyde oxidoreductase, that has been isolated and purified from Nocardia sp. strain NRRL 5646, and to methods of using the carboxylic acid reductase as a biocatalyst for the reduction of carboxylic acids or their derivatives to the corresponding useful product(s). The present invention was begun following an earlier discovery by one of the inventors in a preliminary evaluation based upon whole cell preparations of Nocardia sp. strain NRRL 5646 in which racemic mixtures of ibuprofen were resolved. See, Appl. Environ. Microbiol 60(4):1292 (1994).

Although there have been sporadically published reports of biocatalyzed reduction by the whole cell preparations of a variety of microorganisms, none provide a definitive understanding of the mechanisms involved in the biocatalytic reduction of a carboxylic acid to its aldehyde and alcohol products for industrial use (see, e.g., *Eur. J Biochem.* 8:413 and 420 (1969); and *Eur. J. Biochem.* 31:585 (1972)).

By comparison the present invention provides a carboxylic acid reductase (aryl-aldehyde oxidoreductase) from Nocardia sp. NRRL 5646, purified 196 fold by a combination of Mono-Q, Reactive Green 19 agarose affinity, and hydroxyapatite chromatographies. The purified enzyme runs as a single band of Mr=140 kDa on sodium dodecyl sulfate-polyacrylamide gel electrophoresis. The molecular mass is estimated to be 163±3.8 kDa by gel filtration, indicating that this enzyme is a monomeric protein. The binding of the enzyme to Reactive Green 19 agarose is $Mg^{2+}$ dependent, and the binding capacity was estimated to be about 0.2 mg/ml Reactive Green Agarose in the presence of 10 mM $MgCl_2$. This enzyme catalyzes the reduction of a wide range of aryl carboxylic acids, including substituted benzoic acids, phenyl substituted aliphatic acids, heterocyclic carboxylic acids, and polyaromatic ring carboxylic acids to produce the corresponding aldehydes. The Km values for benzoate, ATP and NADPH were determined to be 645±75 µM, 29.3±3.1 µM, and 57.3±12.5 µM, respectively. Vmax was determined to be 0.902±0.04 µmol/min/mg protein. Km values for S(+)-α-methyl-4-[2-methylpropyl]-benzeneacetic acid (ibuprofen) and its R(−) isomer were determined to be 155±18 µM and 34.5±2.5 µM, respectively. The Vmax for S-(±) and R-(−) isomers were 1.33 µmol/min/mg protein and 0.15 µmol/min/mg protein, respectively. Anthranilic acid is a competitive inhibitor with benzoic acid as substrate with a Ki of 261±30 µM. Moreover, the enzyme has been further identified in terms of its N-terminal amino acid sequence and an internal amino acid sequence of a 76 kDa peptide from a limited α-chymotrypsin digestion.

Thus, the present invention comprises a novel, biologically-derived, carboxylic acid reductase, herein also referred to an aryl-aldehyde oxidoreductase, that has been isolated and substantially purified from Nocardia sp. strain NRRL 5646, and which can be readily distinguished from all previously reported enzymes or proteins, including those from Nocardia or related genera. The broader implications of this discovery include the economical production of products and intermediary by-production of the biocatalytic reduction of carboxylic acids, and an opportunity for the future elucidation of the kinetics involved in biocatalysis.

In a preferred embodiment, the present invention provides the substantially pure biologically-derived, carboxylic acid reductase from Nocardia sp. strain NRRL 5646. As used herein, a protein is said to be "highly purified" or "substantially pure" if the specific activity of the protein cannot be significantly increased by further purification, or if the specific activity is greater than that found in whole cell extracts containing the enzyme.

The terms "carboxylic acid reductase" and "aryl-aldehyde oxidoreductase" are used interchangeably to refer to the enzyme of the present invention, which has been substantially purified from Nocardia sp. NRRL 5646, and characterized. In addition, it is to be understood that throughout this disclosure the carboxylic acid reductase of the present invention is also simply referred to as "the enzyme," and its meaning will be clear in the context in which it is used.

It will be further understood by those skilled in the art that the present invention is not limited to the use of any specific carboxylic acid as the substrate for the biotransformation. Nevertheless, the enzyme will more efficiently produce a corresponding aldehyde product in the presence of certain carboxylic acid starting materials. Although not all inclusive, preferred substrates are exemplified in Table 2, wherein various 2-, 3- and 4-substituted benzoates were examined, including a range of ring-activating and ring-deactivating functional groups. Benzoates substituted with halogens, methyl, methoxy, hydroxy, acetyl, nitro, benzoyl, phenyl, and phenoxyl groups as well as aryl-ring systems containing two (naphthalene) and three (fluorene) rings, and heterocyclic aromatic acids including furoic, nicotinic and indole carboxylic acids were considered; as were cinnamic acid derivatives, phenyl-acetate, phenyl-malonate, phenyl-succinate and 2-phenylpropionic acid.

Of all compounds examined, the best substrates were benzoic acid, 3-bromobenzoic acid, 3-chlorobenzoic acid, 4-fluorobenzoic acid, 4-methylbenzoic acid, 3-methoxybenzoic acid, and 2-naphthoic acid. In general, except for fluoro- and methyl-substituted benzoic acids, it was found that 3-substituted benzoic acids (bromo, chloro, hydroxyl, methoxyl) were the best, substrates within their respective aryl carboxylic acid series. On the other hand, ortho-substituted benzoates were the poorest substrates from among the substrates analyzed. The enzyme efficiently reduces naphthoic acids, but only reduces indole-3-, and indole-5-carboxylic acids. It also reduces furoic acids, nicotinic acid and phenyl-malonate, phenylsuccinate, phenyl-acetate and phenyl-propionate, albeit at slower rates than benzoate itself Nitro-benzoates were not measurably reduced.

A variety of methodologies known in the art can be utilized to obtain the carboxylic acid reductase of the present invention from whole-cell or crude preparations of Nocardia sp. NRRL 5646. One skilled in the art can readily follow known methods for isolating proteins in order to obtain the purified carboxylic acid reducing enzyme. These include, but are not limited to, immunochromatography, size-exclusion chromatography, ion-exchange chromatography, affinity chromatography, HPLC, and the methods set forth by example in the present disclosure. One skilled in the art can readily adapt known purification schemes to delete certain steps or to incorporate additional purification procedures.

In a preferred embodiment affinity chromatography is the selected purification method, offering rapid and high yielding enzyme purification. Dye-ligand chromatography has been successfullly used to purify other nucleotide cofactor requiring enzymes (see, e.g., Clonis, "Dye-ligand chromatography," p. 33, in *Reactive Dyes in Protein and Enzyme Technology.* 1989. Clonis, Atkinson, Bruton., and Lowe (ed.), Stockton Press, New York, N.Y.). Reactive Green 19 gave the best results in purifying the carboxylic acid reductase when compared to Cibacron Blue 3GA, Reactive Blue 4, Reactive Blue 72, Reactive Brown 10, Reactive Green 5, Reactive Red 120, and Reactive Yellow 3 in a preliminary screen.

The dependence of enzyme-ligand binding on the presence of metal ions has been well documented (Clonis et al., *Biochem. J* 197:203–211 (1981); Hughes et al., *Biochim. Biophys.* Acta 700:90–100 (1982)), and in a preferred embodiment of the present invention the binding capacity of the carboxylic acid reductase for Reactive Green 19 was clearly increased with $Mg^{2+}$. The observation that ATP, $NADP^+$, and NADPH each can be used to elute this enzyme suggests that Reactive Green 19 binds to a nucleotide binding site on the enzyme. Moreover, since reactive dyes have been used to map the nucleotide binding sites for other enzymes (Glazer, *J Biol. Chem.* 242(19):4528–4533 (1967); McArdell et al., *Biochem. J* 243:701–707 (1987); McArdell et al., *Biochem. J* 258:715–721 (1989); White et al., *Eur. J Biochem.* 184:89–96 (1989)), it is apparent that Reactive Green 19 may be used to probe the nucleotide binding site(s) of the carboxylic acid reductase.

Most known enzyme-catalyzed carboxylic acid reductions involve carboxylic acid activation with ATP, and subsequent reduction of the resulting mixed anhydride to the aldehyde *Eur. J. Biochem.* 31:585 (1972); *Agric. Biol Chem.* 55(3):757 (1991); Riendeau et al., *J. Biol Chem.* 254(16): 7488–7490 (1979); Rodriguez et al., *J Biol. Chem.* 260(2): 771–774(1985)). However, since the reaction is irreversible, these enzymes (EC 1.2.1.30) are different from the carboxylic acid reductase of the present invention (EC 1.2.1.3), catalyzing the oxidation of aldehydes to carboxylic acids generally with $NAD^+$ as the required cofactor (*Eur. J Biochem.* 8:420 (1969); Small et al., *Eur. J Biochem.* 128:119–123 (1982)).

Numerous other properties distinguish the carboxylic acid reductase of the present invention from any previously identified enzymes. As described in Example 1, the native molecular weight of the carboxylic acid reductase was estimated by gel filtration chromatography to be 163.3±4.8 kDa (n=3). By SDS-PAGE, the denatured molecular weight was estimated to be 140 kDa (FIG. 2), indicating that the active enzyme is a monomer. Thus, the molecular weights of the present enzyme appear similar to those reported by Kato et al., (*Agric. Biol. Chem.* 55(3):757 (1991)), and by Gross et al. for the enzyme from Neurospora crassa (*Eur. J. Biochem.* 8:413 (1969)). By UV visible spectroscopy, the purified enzyme displayed only two absorption maxima at 214 and 283 nm, indicating the lack of prosthetic groups such as a flavin or heme. However, the apparent Km values for benzoate, ATP and NADPH are more than 1000 fold higher for the carboxylic acid reductase of the present invention than the Km values reported for the enzyme from Nocardia asteroides by Kato et al., (*Agric. Biol. Chem.* 55(3):757 (1991)). Furthermore, in contrast to the present enzyme, the Km of benzoate for the oxidoreductase from Neurospora crassa is 63 µM and its activity can be inhibited by benzoate at 300 µM (*Eur. J Biochem.* 8:413 (1969)). In contrast, no inhibition was observed for the present enzyme, even when the benzoate concentration reached 2 mM (see Example 1), demonstrating the differences in the catalytic properties of the carboxylic acid reductase as compared with those of previously reported enzymes.

Moreover, the carboxylic acid reductase is mechanistically distinguished from a known fatty acid reducing enzyme involved in chemoluminescence, even though each produces an aldehyde by a method requiring initial AMP activation of carboxylic acids and subsequent transacylation to a Cys residue within the active site (Rodriguez et al., *J Biol. Chem.* 260(2):771–774(1985)). The fatty acid reducing enzyme requires FMN as a cofactor in subsequent carbonyl reduction reactions, whereas by comparison, the UV spectrum for the Nocardia carboxylic acid reductase contains characteristic absorption peaks only for peptides, demonstrating an absence of the flavin requirement in the present reaction.

Definitive identification of the carboxylic acid reductase lies in its amino acid sequence, and ultimately in the nucleotide sequence encoding the active enzyme. Consequently, selecting from among the many known methods in the art for sequence analysis, the N-terminal amino acid sequence and an internal amino acid sequence were determined by Edman degradation in duplicate analyses of two separately purified samples of the enzyme. The N-terminal amino acid sequence is $H_2N$-Ala-Val-Asp-Ser-Pro-Asp-Glu-Arg-Leu-Gln-Arg-Arg-Ile-Ala-X-Leu. The internal sequence, determined with a 76 kDa peptide from α-chymotrypsin digestion, is Lys-Leu-Ser-Gln-Gly-Glu-Phe-Val-Ala-His-Leu-X-Ala-Val. Using the BLASTP and TBLASTN computer programs (Altschul et al., *J. Mol. Biol.* 215:403–410 (1990)) to search the updated SwissProt, Genpept, GenBank, and EMBL databases, no matching known amino acid sequence was found corresponding to the carboxylic acid reductase.

Yet another embodiment of the invention provides a method (exemplified in FIG. 1) of biocatalytically reducing a carboxylic acid, or a derivative thereof, to its corresponding product(s), comprising using a substantially purified, biologically-derived carboxylic acid reductase, as exemplified by that which is isolated from Nocardia sp. strain NRRL 5646. A preferred embodiment provides a method of biocatalytically reducing a carboxylic acid, or a derivative thereof, to its corresponding product(s), comprising the steps of: a) mixing an effective amount of the substantially purified, biologically-derived carboxylic acid reductase with the carboxylic acid, or its derivative, to activate reduction; b) incubating the mixture for a period of time to achieve reduction of the carboxylic acid, or its derivative into the corresponding product(s); and c) extracting the product(s). See, FIG. 1.

In a preferred embodiment of the invention the extracted product of the biocatalytic method of reducing a carboxylic acid by the substantially purified carboxylic acid reductase is its corresponding aldehyde product(s). See, FIG. 1. Thus, in another preferred embodiment of the invention the aldehyde product(s) is provided, produced by the biocatalytic action of the substantially purified carboxylic acid reductase on a carboxylic acid starting material, or on a derivative thereof Synthesis of the intermediary by-products by the present method provides an economic alternative starting material for subsequent reactions. For example, a readily available source of carbonyl phosphates bypasses the need for expensive cofactors in the reduction reaction, such as ATP.

In a particularly preferred embodiment of the invention a particular aldehyde, vanillin, is produced by the biocatalytically activated reduction of vanillic acid, or a precursor or derivative thereof, by the substantially purified, biologically-derived carboxylic acid reductase from Nocardia sp. strain NRRL 5646. See, FIG. 7. Another particularly preferred embodiment of the invention provides a method of biocatalytically reducing vanillic acid, or a precursor or derivative thereof, to vanillin, comprising the steps of: a) mixing an effective amount of the substantially purified, biologically-derived carboxylic acid reductase with the vanillic acid or, a precursor or derivative thereof, and cofactors to activate reduction; b) incubating the mixture for a period of time to achieve reduction of the vanillic acid, or its precursor or derivative into the vanillin; and c) extracting the vanillin product. See, FIG. 7.

In yet another particularly preferred embodiment of the invention vanillin is provided which has been produced by the biocatalytic action of the substantially purified carboxylic acid reductase on vanillic acid, or on a precursor or derivative thereof. See, FIG. 7.

Although vanillic acid is a preferred substrate for the biocatalytic production of vanillin in one embodiment of the invention, the starting material can be any suitable benzoid precursor, having derivatives at the 1-position of 4-hydroxy-3-methylbenzene, such as, e.g., ferulic acid or isoeugenol. Thus, the present invention also includes methods for the production of an aldehyde, such as vanillin, from such suitable benzoid precursors.

Ferulic acid (3-(4-hydroxy-3-methoxyphenyl)-propenoic acid) is an extremely abundant plant product available in more than 2% yield (wt/wt) (more than 1 billion pounds available annually) from the hulls of corn kernels obtained from wet milling (Rosazza et al. *J. Ind. Microbiol* 15:457–471 (1995)). Elimination of two carbons from the cinnamoyl chain is one of the most common reactions for ferulic acid biotransformation, and vanillic acid is one of the major metabolites obtained by ferulic acid biotransformation by species of Bacillus (Gurujeyalakshmi et al., *Current Microbiol* 16:69–73 (1987)), Pseudomonas (Jurkov et al., *FEMS Microbiol Lett.* 111:245–250 (1993); Toms et al., *Biochemistry* 9:337–343 (1970)), Polyporus (Ishikawa et al., *Archiv. Biochem. Biophys.* 100:140–149 (1963)), Rhodotorula (Huang et al., *J Biol. Chem.* 268:23954–23958 (1993)), and Streptomyces (Sutherland et al., *Can. J Microbiol.* 29:1253–1257 (1983)). However, the vanillin yields observed in the reported microbial transformations of ferulic acid were very low, and vanillic acid was not the sole product.

On the other hand, it has been reported that more than 90% of ferulic acid was converted to vanillic acid by R. rubra IFO 889 by a β-oxidation process (*J. Biol. Chem.* 268:23954 (1993)). Thus, vanillic acid affords an extremely abundant, natural substrate for the production of vanillin. The transformation from vanillic acid to vanillin with ATP and NADPH, catalyzed by the substantially purified carboxylic acid reductase is quantitative, further establishing the feasibility of vanillin from vanillic acid directly with this enzyme by the mechanism shown in FIG. 7.

The rate of the reduction operation may be increased by known methods, such as substrate modification, which may also prevent unwanted reactions. For example, in the case of vanillic acid, it has been demonstrated that the increase in the rate of carboxylic acid reduction as a result of o-benzylation is more than 15 fold when the substrate concentration is 5 mM (unpublished data).

In another embodiment of the invention, the carboxylic acid reductase may be purified from cells which have been altered to express the desired enzyme. As used herein, a cell is said to be "altered to express a desired protein" when the cell, through genetic manipulation, is made to produce a protein which it normally does not produce, or which the cell normally produces at low levels. One skilled in the art can readily adapt procedures for introducing and expressing either genomic or cDNA sequences into either eukaryotic or prokaryotic cells, in order to generate a cell which produces the desired carboxylic acid reductase.

The present invention further encompasses the expression of the carboxylic acid reductase (or a chemical or functional derivative, analog or variant thereof) in either prokaryotic or eukaryotic cells, naturally or recombinantly. A "functional derivative" of a sequence, either protein or nucleic acid, is a molecule that possesses a biological activity (functional or structural) that is substantially similar to a biological activity of the protein or nucleic acid sequence, but which may contain post-translational modifications such as covalently linked carbohydrate, depending on the necessity of such modifications for the performance of a specific function. A molecule is said to be a "chemical derivative" of another molecule when it contains additional chemical moieties not normally a part of the molecule, such as those which may be added, e.g., to improve the molecule's solubility, absorption, biological half life, and the like, or to decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

A "variant" or "allelic or species variant" of an enzyme or protein is meant to refer to a molecule substantially similar in structure and biological activity to either the protein or nucleic acid. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Preferred prokaryotic hosts include bacteria such as *E. coli*, Bacillus, Streptomyces, Pseudomonas, Salmonella, Serratia, etc. Under such conditions, the enzyme will not be glycosylated. The prokaryotic host must be compatible with the replicon and control sequences in the expression plasmid.

However, prokaryotic systems may not prove efficacious for the expression of all proteins. While prokaryotic expression systems, e.g., pET3c, have been used to express high molecular weight proteins, such as a biologically active (molecular weight ($M_r$) ~118 kDa) FGF-1: β-galactosidase chimera, successful folding and disulfide bond formation may be difficult to accomplish in bacteria. Nevertheless, to express an enzyme in a prokaryotic cell, it is necessary to operably link the carboxylic acid reductase coding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase, and the ζ-28-specific promoters of B. subtilis, the promoters of the bacteriophages of Bacillus, and Streptomyces promoters. See, e.g., reviews by Glick (*J Ind. Microbiol.* 1:277–282 (1987)); Cenatiempo (Biochimie 68:505–516 (1986)); and Gottesman (*Ann. Rev. Genet.* 18:415–442 (1984)). Proper expression in a prokaryotic cell also requires the presence of a ribosome binding site upstream of the gene sequence-encoding sequence, as recognized in the art.

Preferred eukaryotic hosts include yeast, fungi, insect cells, mammalian cells, either in vivo or in tissue culture. For a eukaryotic host, several possible vector systems are available for the expression of the carboxylic acid reductase. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression, or in conjunction with expressed products. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Yeast expression systems can also carry out post-translational peptide modifications. A number of recombinant DNA strategies exist which utilize strong promoter sequences and high copy number of plasmids which can be utilized for production of the desired proteins in yeast. Any of a series of yeast gene sequence expression systems incorporating promoter and termination elements from the actively expressed gene sequences coding for glycolytic enzymes produced in large quantities when yeast are grown in mediums rich in glucose can be utilized.

An alternative host for a protein the size of the carboxylic acid reductase enzyme is an insect cell, for example the Drosophila larvae in conjunction with the baculovirus insect cell expression system.

As is widely known, translation of eukaryotic mRNA is initiated at the codon which encodes the first methionine. For this reason, it is preferable to ensure that the linkage between a eukaryotic promoter and a DNA sequence encoding the carboxylic acid reductase does not contain any intervening codons which are capable of encoding a methionine (i.e., AUG). The presence of such codons results either in a formation of a fusion protein (if the AUG codon is in the same reading frame as the enzyme coding sequence) or a frame-shift mutation (if the AUG codon is not in the same reading frame as the enzyme coding sequence).

The carboxylic acid reductase coding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the enzyme may occur through the transient expression of the introduced sequence. Alternately, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Many prokaryotic and eukaryotic plasmids are known in the art.

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of the carboxylic acid reductase or active fragments thereof. This can take place in the transformed cells per se, or following the induction of these cells to differentiate.

In certain preferred embodiments of the invention, such as the biotransformation of vanillic acid or its precursors into vanillin, it is important that the enzyme be considered safe for use in food product, particularly for food to be consumed by humans. Consequently, it is essential in such situations that carboxylic acid reductase be produced from and/or used in a GRAS approved host, so that the aldehyde product of the bioconversion may also be considered safe.

Since highly purified proteins are now available, X-ray crystallography and NMR-imaging techniques can be used to identify the structure of the enzyme. Utilizing such information, computer modeling systems are now available that allows one to "rationally design" an agent capable of binding to a defined structure. As used herein, an agent is said to be "rationally designed" if it is selected based on a computer model of the carboxylic acid reductase.

In yet another embodiment of the present invention, methods are provided for modulating the recovery of the aldehyde product by altering or blocking the translation of RNA encoding the de hydrogenase enzyme which transforms the desired aldehyde product into alcohol before it can be recovered. Specifically, said method comprises introducing into a cell a DNA sequence which is capable of transcribing RNA which is complimentary to the RNA encoding the dehydrogenase enzyme which converts the aldehyde into alcohol. By introducing such a DNA sequence into a cell, an antisense RNA will be produced which will hybridize and block the translation of the competing enzyme. By controlling the level of transcription of antisense RNA, one skilled in the art can essentially regulate the level of activity of the enzymes. Such antisense cloning has been recognized for many years.

All essential publications mentioned herein are hereby incorporated by reference.

In order that those skilled in the art can more fully understand this invention, the following examples are set forth. These examples are included solely for the purpose of illustration, and should not be considered as expressing limitations unless so set forth in the appended claims.

Examples

In the following examples and protocols, all commercially available reagents were utilized in accordance with the manufacturer's recommendations. The cell and protein purification methods utilized in this application are established in the art and will not be described in detail. Methodologic details may be readily derived from the cited publications. Unless otherwise stated, reagents were purchased from Sigma Chemical Co. (St. Louis, Mo.) and Aldrich Chemical Co. (Milwaukee, Wis.).

Example 1

Purification, Isolation and Characterization of a Carboxylic Acid Reductase from Nocardia sp. NRRL 5646

Purification and Isolation of the Enzyme

Preparation of cell free extracts. Nocardia species NRRL 5646 is maintained in the University of Iowa, College of Pharmacy culture collection. It is grown and maintained on slants of Sabouraud-dextrose agar or sporulating agar (ATCC No.5 medium).

Shaken flask cultures were grown by a standard two stage incubation protocol (Betts et al., *J Med. Chem.* 17:599–602 (1974)) in 200 ml of sterile medium held in stainless steel-capped 1-liter DeLong culture flasks. The medium, containing (wt/vol) 2% glucose, 0.5% yeast extract, 0.5% soybean flour, 0.5% NaCl, and 0.5% $K_2HPO_4$ in distilled water, was adjusted to pH 7.2 with 6N HCl, and then autoclaved at 121° C. for 20 min. Cultures were incubated by shaking at 250 rpm at 28° C. on New Brunswick Scientific, C25 Gyrotory shakers. A 10% inoculum derived from a 72-hour first-stage culture was used to initiate the second-stage culture, which was incubated as before. After 24 hours incubation in the second stage, benzoic acid was added to a concentration of 5 mg/ml as an inducer for enzyme synthesis. The culture was harvested 24 hours after the addition of benzoate, the cells were collected from the medium by centrifugation at 8,000×g for 20 min., and washed twice with 0.9% NaCl. Cell pellets were stored at −38° C. until needed. Ty For preparation of cell free extracts, 25 g (wet weight) of cell pellet was suspended in 150 ml of cold 50 mM Tris-HCl buffer (pH 7.5) containing 1 mM dithiothreitol (DTT), 0.1 mM phenylmethyl sulfonyl fluoride (PMSF), 1 mM EDTA, and 10% (v/v) glycerol. The cell suspension was disrupted with a Sonifier Cell Disrupter 350 (Branson Sonic Power Co., Danbury, Conn.) at 250 W with 20% intermittent duty cycle for 10 min. Cell debris was removed by centrifugation at 100,000×g for 40 min at 4° C. The 100,000×g supernatant was used directly for subsequent enzyme purification steps, which were all conducted at 4° C.

As a result, it was determined that the specific activity of aryl aldehyde oxidoreductase in crude extracts of Nocardia sp. NRRL 5646 could be induced up to 10 fold by the addition of up to 5 mg/ml benzoate to the 24 hour, stage two cultures.

Enzyme assay

The standard aryl-aldehyde oxidoreductase assay solution contained 0.15 mM NADP, 1 mM ATP, and 5 mM sodium benzoate, 10 mM $MgCl_2$ and 0.01 to 0.3 units of enzyme in 50 mM Tris-HCl buffer in a final volume of 0.7 ml. The reference cuvette contained all components except for benzoate. Enzyme reactions were initiated by adding enzyme, and they were monitored by recording the absorption decrease at 340 nm at 25° C. with a Shimadzu 160 spectrophotometer. One unit of the carboxylic acid reductase (aryl-aldehyde oxidoreductase) is defined as the amount of enzyme that catalyzes the reduction of 1 μmol benzoate to benzaldehyde per min. under standard assay conditions.

Protein assay

The concentration of protein was measured by the Bradford protein microassay (Bradford, *Anal Biochem.* 72:248–254 (1976)), with bovine serum albumin as the standard.

Enzyme purification

Crude 100,000×g supernatants (170 ml, approximately 500 mg protein) were applied to a Mono-Q column (2×20 cm) from Bio-Rad (Hercules, Cailf.) preequilibrated with 50 mM Tris-HCl (pH 7.5) containing 1 mM DTT, 1 mM EDTA, 0.1 mM PMSF and 10% (v/v) glycerol. The column was washed with 60 ml of starting buffer before the enzyme was eluted with a 0–1M NaCl linear gradient (400 ml) in starting buffer while fractions of 5 ml were collected. The active fractions (fractions 22–28) were combined, concentrated to 15 ml in an Amicon concentrator (PM-30 membrane). This preparation was diluted with 200 ml of 20 mM Tris-HCl buffer (pH 7.5) containing 1 mM DTT, 10 mM MgCl2 and 10% (v/v) glycerol, and concentrated to 50 ml for the next step.

The enzyme was loaded onto a Reactive Green 19 agarose column (2×10 cm) preequilibrated with 20 mM Tris-HCl buffer (pH 7.5) containing 1 mM DTT, 10 mM $MgCl_2$, and 10% (v/v) glycerol. The column was washed with 30 ml of starting buffer and eluted with 100 ml of the Tris-HCl buffer with a combined linear gradient of EDTA (0–2 mM) and $NADP^+$ (0–0.5 mM) and $NADP^+$ (−0.5 mM) (200 ml) while 2.5 ml fractions were collected. The active fractions (fractions 9–14) were combined, concentrated with an Amicon concentrator (PM 30 membrane) to 5 ml, and diluted to 50 ml with 5 mM phosphate buffer (pH 6.8) containing 1 mM DTT, 5 mM $MgCl_2$ and 10% (v/v) glycerol.

This preparation was then loaded onto a hydroxyapatite column (0.8×5 cm) (Bio-Rad, Hercules, Cailf.) equilibrated with 5 mM phosphate buffer, pH 6.8. The column was next washed with 20 ml of starting buffer. The enzyme was eluted with a linear gradient from 5 mM to 80 mM phosphate buffer (80 ml). Fractions 44–52 (FIG. 2) were combined for analysis.

The results of a typical purification of Nocardia species carboxylic acid reductase (aryl-aldehyde oxidoreductase) are summarized in Table 1.

TABLE 1

Purification of the Carboxylic Acid Reductase

| Steps | Total protein (mg) | Total Activity (Units) | Specific Activity (U/mg) | Yield (%) | Purification (fold) |
|---|---|---|---|---|---|
| Crude Extract | 382 | 11.3 | 0.03 | 100 | 1 |
| Mono-Q | 66.8 | 8.15 | 0.12 | 72 | 4 |
| Reactive Green 19 | 3.83 | 6.54 | 1.71 | 58 | 57 |
| Hydroxyapatite | 1.03 | 6.05 | 5.89 | 53 | 196 |

Because the binding capacity of the enzyme to immobilized Reactive Green 19 was dependent upon the concentration of $Mg^{++}$, and clearly increased by its presence, 10 mM $MgCl_2$ was included in chromatographic buffers in this step. The binding capacity of immobilized Reactive Green 19 in 20 mM Tris-HCl, pH 7.5 containing 10 mM $MgCl_2$ was determined to be 200 μg of the enzyme preparation from mono-Q step/ml Reactive Green Agarose. The enzyme could be eluted with 0.1M NaCl, 5 mM EDTA, 0.5 mM NADPH, 1 mM ATP, and 0.5 mM $NADP^+$, independently, suggesting that Reactive Green 19 binds to a nucleotide binding site on the enzyme. However, a mixture of $NADP^+$ and EDTA to elute the enzyme gave enzyme preparations of the highest specific activity.

Figure 2:
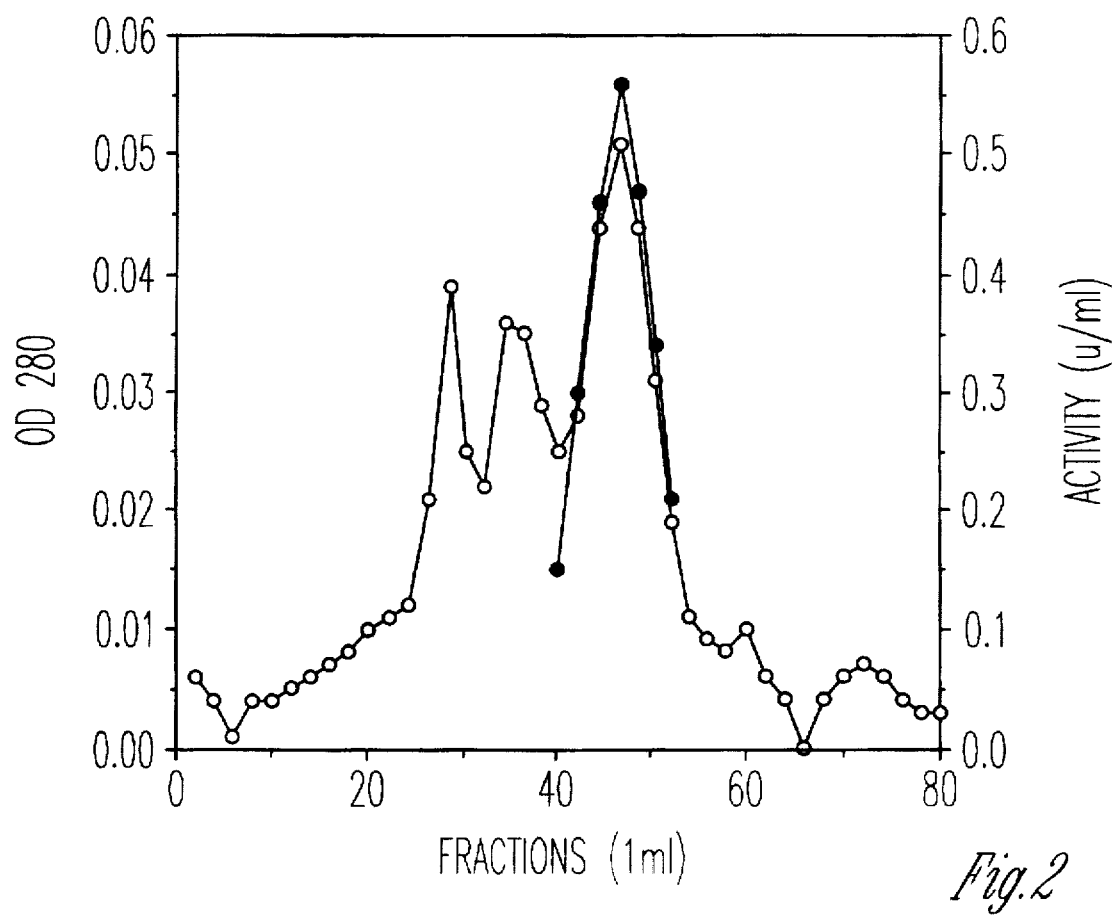
FIG. 2 depicts the elution profile of the carboxylic acid reductase, or aryl-aldehyde oxidoreductase, from a hydroxyapatite column with a linear gradient of phosphate buffer (pH 6.8) at concentrations from 5 mM to 80 mM. Open Circles (○), O.D. 280 nm; closed circles (●), enzyme activity.

In the hydroxyapatite purification step, elution with 5–80 mM phosphate gave three major eluted peaks (FIG. 2). Aryl aldehyde oxidoreductase activity corresponded to fractions 46–52. SDS-PAGE results (FIG. 3, lane 2) showed that the purity of this preparation was higher than 95%.

Purified carboxylic acid reductase (aryl-aldehyde oxidoreductase) had a specific activity of 5.9 units/mg of protein. This represented a 196 fold purification from crude extracts, with 53% recovery of total enzyme activity. By this purification, it was determined that soluble carboxylic acid reductase (aryl aldehyde oxidoreductase) represents approximately 0.5% of the total protein in crude extract.

The purification procedure was highly reproducible, affording 1 mg of pure enzyme in each purification by this method.

Characterization of the Enzyme

The effect of $Mg^{++}$ on the binding of carboxilic acid reductase (aryl-aldehyde oxidoreductase) to Reactive Green Agarose. Five 2.5 ml prepacked Reactive Green 19 agarose columns (Sigma Chemical Co.) were equilibrated with 1, 3, 5, 7, and 10 mM $MgCl_2$, respectively, in 20 mM Tris-HCl buffer (pH 7.5) containing 1 mM DTT, and 10% glycerol. The enzyme preparation from the Mono-Q step was equilibrated with appropriate buffers and loaded onto the corresponding columns. The enzyme was eluted with 1M NaCl after the columns were washed with 2.5 ml of starting buffers. The amount of enzyme bound to the column was expressed as the percentage of that in which 10 mM $MgCl_2$ was in the buffer.

SDS-PAGE

Sodium dodecyl sulfate-polyacrylamide gel electrophoresis (SDS PAGE) was performed with a Bio-Rad Mini-Protein II dual-slab cell with a discontinuous buffer system (Laemmli, Nature (London) 227:680–685 (1970)), and an 8% separation gel. Gels were stained with Coomassie Blue. Protein standards used to estimate the subunit molecular masses were myosin (208 kDa), β-galactosidase B (107 kDa), phosphorylase b (107 kDa), bovine serum albumin (79.5 kDa), and ovalbumin (49.5 kDa) (BioRad, Hercules, Cailf.)

Native molecular weight determination

Analytical gel filtration chromatography was carried out with an Alltech Macrosphere 150 column (7 µm, 0.46 by 25 cm). The mobile phase of 0.3M phosphate buffer, pH 7.0 was used to equilibrate the column and to elute protein samples at a flow rate of 0.2 ml/min. Eluted protein peaks (retention volumes, $R_v$) were monitored at 280 nm. The standard proteins ($M_r$) were apoferritin (443 kDa, $R_v$=1.91 ml), β amylase (200 kDa, $R_v$=2.11 ml), alcohol dehydrogenase (150 kDa, $R_v$=2.22 ml), and bovine serum albumin (66 kDa, $R_v$=2.33 ml) (BioRad).

Analysis of the N-terminal amino sequence and internal amino acid sequence

The N-terminal amino acid sequence was determined by Edman degradation and analysis in an automated sequencer (Genetic Engineering Facility, University of Illinois at Urbana-Champaign, Urbana, Ill.).

Protein cleavage for peptide mapping was carried out with 25 ng α-chymotrypsin (C 7762, Sigma) digestion of 25 µg purified enzyme in 50 µl 50 mM $(NH_4)_2CO_3$, pH 8.5 at 15° C. for 7 hr. The resulting peptides were separated with 10% SDS PAGE. The separated peptides were transferred to polyvinyldiflouride (PVDF) membrane (Applied Biosystems, Foster City, Cailf.) by electroblotting in 10 mM 3-[cyclohexylamino]-1-propane-sulfonic acid, pH 11 containing 10% methanol at 50 v for 7 h. Peptide bands were visualized with 0.1% Coomassie Blue R-250 staining in 40% methanol. A peptide of 76 kDa was selected for N-terminal amino acid sequence determination by Edman degradation (Protein Facility, The University of Iowa, Iowa City, Iowa.).

Absorption spectrum of aryl-aldehyde oxidoreductase

The UV-visible absorption spectrum of the aryl aldehyde oxidoreductase (100 µg in 0.7 ml of 50 mM Tris-HCl buffer, pH 7.5) was recorded with a Sim-Aminco model DW2000 UV-visible spectrometer with 0.7 ml cuvettes. The spectrum was scanned over the range of 200 to 600 nm.

Substrate specificity of the carboxylic acid reductase (aryl aldehyde oxidoreductase)

Crude enzyme preparations consisting of 100,000×g supernatants were used in this study. A substrate concentration of 5 mM was established for each carboxylic acid derivative in 50 mM Tris-HCl, pH 7.5 containing 0.15 mM NADPH and 1 mM ATP. The relative rate of reduction for each carboxylic acid derivative is expressed as the percentage of the initial rate of benzoate reduction. Typically, the rate of benzoate reduction was 0.066 $\Delta A_{340}$/min., which is equivalent to 10.6 µM/min.

Properties of the carboxylic acid reductase (aryl-aldehyde oxidoreductase)

Inclusion of 10% glycerol in all chromatographic buffers was used to stabilize the enzyme. Nevertheless, the purified enzyme in 50 mM pH 7.5 Tris-HCl buffer, containing 10% glycerol, lost nearly 25% of its activity in 8 hr at 4° C.

Figure 3:
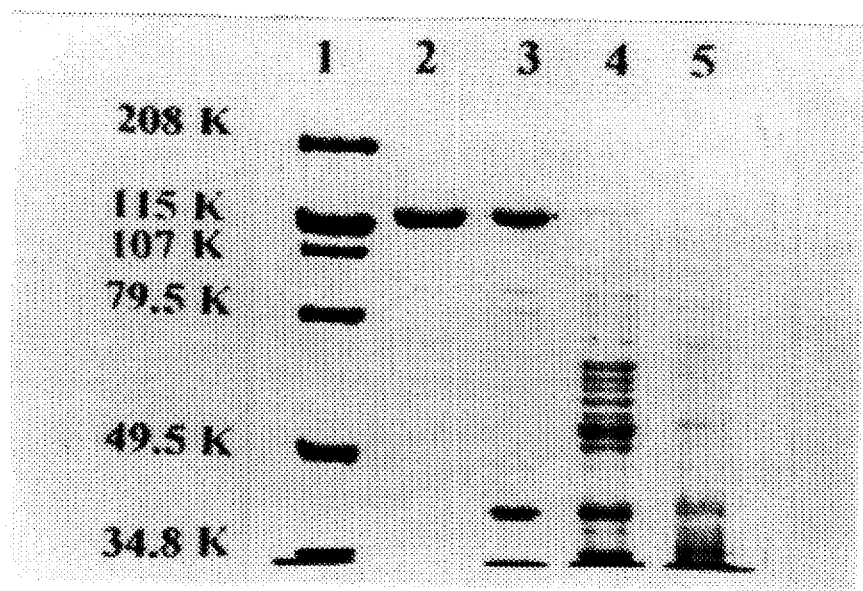
FIG. 3 depicts the SDS-PAGE analysis of the samples taken during the purification of the carboxylic acid reductase (aryl-aldehyde oxidoreductase). Lane 1: molecular weight markers. Lane 2: hydroxyapatite column fractions of the enzyme. Lane 3: Reactive Green 19 column fractions of the enzyme. Lane 4: mono-Q column fractions of the enzyme. Lane 5: crude extract. About 2.5 mg of protein was loaded into each lane.

The native molecular weight was estimated by gel filtration chromatography to be 163.3 ±4.8 kDa (n=3). By SDS-PAGE, the denatured molecular weight was estimated to be 140 kDa (FIG. 3). Thus, the active enzyme appears to be a monomer. By UV visible spectroscopy, the purified enzyme displayed only two absorption maxima at 214 and 283 nm, indicating the lack of prosthetic groups such as a flavin or heme.

The N-terminal amino acid sequence and an internal amino acid sequence were determined by Edman degradation in duplicate analyses of two separately purified samples. The N-terminal amino acid sequence is $H_2$N-Ala-Val-Asp-Ser-Pro-Asp-Glu-Arg-Leu-Gln-Arg-Arg-Ile-Ala-X-Leu. The internal sequence determined with a 76 kDa peptide from α-chymotrypsin digestion is Lys-Leu-Ser-Gln-Gly-Glu-Phe-Val-Ala-His-Leu-X-Ala-Val. The BLASTP and TBLASTN programs (Altschul et al., *J. Mol. Biol.* 215:403–410 (1990)) were used to search the updated SwissProt, Genpept, GenBank, and EMBL databases. No matching amino acid sequences were found.

The range of oxidoreductase activities of crude, 100,000×g Nocardia extract with a variety of substrates was investigated. Various substituted 2-, 3- and 4-substituted benzoates were examined, including a range of ring-activating and ring-deactivating functional groups. Benzoates substituted with halogens, methyl, methoxy, hydroxy, acetyl, nitro, benzoyl, phenyl, and phenoxyl groups as well as aryl-ring systems containing two (naphthalene) and three (fluorene) rings, and heterocyclic aromatic acids including furoic, nicotinic and indole carboxylic acids were considered. In addition, one cinnamic acid derivative, phenylacetate, phenyl-malonate, phenyl-succinate and 2-phenylpropionic acid were studied. The calculated relative activities (substrate specificities) of the carboxylic acid reductase from Nocardia sp. NRRL 5646 with the exemplary substrates are summarized in Table 2.

TABLE 2

Substrate Specificity of Crude Carboxylic Acid Reductase from Nocardia sp. NRRL 5646

| Substrate | Relative Activity | Substrate | Relative Activity |
|---|---|---|---|
| benzoic acid | 100 | 2-nitro-benzoic acid | 0 |
| 2-bromo-benzoic acid | 5 | 3-nitro-benzoic acid | 0 |
| 3-bromo-benzoic acid | 105 | 4-nitro-benzoic acid | 0 |

TABLE 2-continued

Substrate Specificity of Crude Carboxylic Acid Reductase from Nocardia sp. NRRL 5646

| Substrate | Relative Activity | Substrate | Relative Activity |
|---|---|---|---|
| 4-bromo-benzoic acid | 72 | 2-benzoyl-benzoic acid | 0 |
| 2-chloro-benzoic acid | 3 | 3-benzoyl-benzoic acid | 53 |
| 3-chloro-benzoic acid | 124 | 4-benzoyl-benzoic acid | 6 |
| 4-chloro-benzoic acid | 100 | 2-phenyl-benzoic acid | 16 |
| 2-fluoro-benzoic acid | 57 | 4-phenyl-benzoic acid | 21 |
| 3-fluoro-benzoic acid | 78 | 2-phenoxy-benzoic acid | 0 |
| 4-fluoro-benzoic acid | 94 | 4-phenoxy-benzoic acid | 11 |
| 2-toluic acid | 6 | 1-naphthoic acid | 77 |
| 3-toluic acid | 4 | 2-naphthoic acid | 95 |
| 4-toluic acid | 82 | fluorene-1-carboxylic acid | 17 |
| 3-methoxy-cinnamic acid | 8 | indole-2-carboxylic acid | 0 |
| 2-hydroxyl-benzoic acid | 0 | indole-3-carboxylic acid | 2 |
| 3-hydroxyl-benzoic acid | 77 | indole-4-carboxylic acid | 0 |
| 4-hydroxyl-benzoic acid | 6 | indole-5-carboxylic acid | 10 |
| 2-anisic acid | 3 | 2-furoic acid | 18 |
| 3-anisic acid | 87 | 3-furoic acid | 22 |
| 4-anisic acid | 36 | nicotinic acid | 5 |
| 2-acetyl-benzoic acid | 4 | phenyl malonic acid | 3 |
| 4-acetyl-benzoic acid | 20 | phenyl succinic acid | 11 |
| 2-acetylamino-benzoic acid | 0 | phenyl acetic acid | 43 |
| 4-acetylamino-benzoic acid | 22 | 2-phenyl propionic acid | 16 |

Except for fluoro and methyl substituted benzoic acids, it was found that 3-substituted benzoic acids (bromo, chloro, hydroxyl methoxyl) were the best substrates within their respective aryl carboxylic acid series. In general, ortho-substituted benzoates were the poorest substrates from within any of the substrates compared. The oxidoreductase from Nocardia sp. NRRL 5646 efficiently reduces naphthoic acids, but only reduces indole-3-, and indole-5-carboxylic acids. The enzyme also reduces furoic acids, nicotinic acid and phenyl-malonate, phenylsuccinate, phenyl-acetate and phenyl-propionate, albeit at slower rates than benzoate itself. Of all the compounds examined, the best substrates were determined to be benzoic acid, 3-bromobenzoic acid, 3-chlorobenzoic acid, 4-fluorobenzoic acid, 4-methylbenzoic acid, 3-methoxy-benzoic acid, and 2-naphthoic acid. Nitro-benzoates were not reduced at all.

Kinetic constants were obtained by fitting experimental data with the EZ-FIT program developed by Perrella (Perrella, Anal. Biochem. 174:437–447 (1987)). All data are the mean of three determinations (see Table 3).

TABLE 3

Kinetic Properties of the Carboxylic Acid Reductase

| Substrate, Cofactors, or Inhibitor | $K_m$ (µM) | $V_{max}$ (µmol/min/mg of protein) | $K_i$ (µM) |
|---|---|---|---|
| benzoic acid | 645 ± 75 | 0.902 ± 0.04 | |
| ATP | 57.3 ± 12.5 | | |
| NADPH | 29.3 ± 3.1 | | |
| anthranilic acid | | | 261 ± 30 |
| S(+)-ibuprofen | 155 ± 18 | 0.148 ± 0.003 | |
| R(−)-ibuprofen | 34.5 ± 2.5 | 1.33 ± 0.02 | |

With the purified aryl aldehyde oxidoreductase, kinetic properties were determined using S(+)- and R(−)-ibuprofen isomers (Table 3). S(+)-α-Methyl-4-[2-methylpropyl]-benzeneacetic acid (ibuprofen) was from Aldrich Chemical Co. R(−) isomer of ibuprofen was a gift from Dr. Ching-Shih Chen, University of Rhode Island (Chen et al., Biochim. Biophys. Acta 1033:1–6 (1990)). For the R(−) isomer, $K_m$ and $V_{max}$ were 34.5±2.5 µM and 1.33+0.02 µmol/min/mg of protein, respectively. For the S(+) isomer, $K_m$ and $V_{max}$ were 155±18 µM and 0.148±0.003 µmol/min/mg of protein, respectively. Assuming the enzyme was pure and only one active site exists in each enzyme molecule, the turn-over number for S(+) and R(−) ibuprofen isomers were calculated to be 186 min$^{-1}$, and 21 min$^{-1}$, respectively. Substrate enantiopurities were checked by specific rotation determination for each isomer (Chen and Rosazza, Appl. Environ. Microbiol. 60(4):1292–1296 (1994)).

Figure 4:
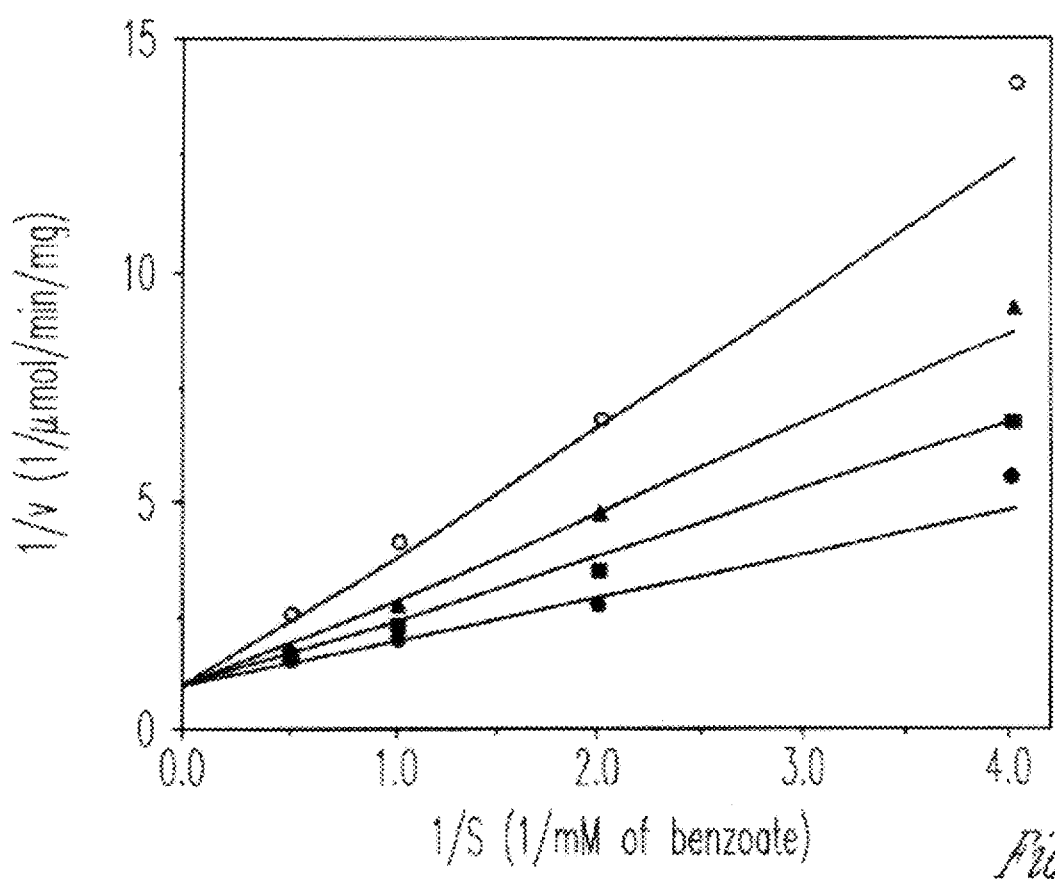
FIG. 4 Double reciprocal plots of the inhibition of the carboxylic acid reductase (aryl-aldehyde oxidoreductase) by anthranilic acid. The inhibition experiments were carried out as for standard enzyme assays under initial velocity conditions. Each data point represents the mean of four measurements: closed circles (●), 0 mM anthranilic acid; closed squares (■), 125 mM anthranilic acid; closed triangles (▲), 250 mM anthranilic acid; open circles (○), 500 mM anthranilic acid.

Under pseudo-first order reaction conditions, the turnover number for benzoate was 126 min$^{-1}$. This enzyme did not reduce benzaldehyde to benzyl alcohol. When 5 mM 2-amino benzoic acid (anthranilic acid) was used instead of benzoic acid in the enzyme assay solution, no NADPH oxidation was observed. Inhibition studies revealed that 2-amino benzoic acid was a typical competitive inhibitor to benzoic acid (see FIG. 4). The rate of NADPH (0.15 mM) reduction of synthesized benzoyl AMP (0.35 mM) in 50 mM Tris-HCl, pH 7.5, by the purified enzyme was similar to the rate observed when benzoate was the substrate under enzyme assay conditions.

Therefore, it appears that mechanistically the carboxylic acid reductase enzyme requires ATP, benzoic acid, and NADPH to catalyze the two reaction steps: conversion of benzoate to benzoyl-AMP; and reduction of benzoyl-AMP to benzaldehyde. The fact that the synthetically prepared benzoyl-AMP was reduced by the enzyme when NADPH was added in the absence of ATP, supports this conclusion.

Benzoyl AMP was synthesized by reacting 36 mg benzoic acid with 50 mg N,N'-carbonyldiimidazole in 10 ml anhydrous DMF at room temperature for 2 hours to form benzoyl imidazole in almost quantitative yield. AMP (100 mg), 20 ml DMF, and 0.1 ml of 0.5% pyridine in DMF were added to the reaction mixture which was stirred at room temperature for 72 hours to give benzoyl AMP [TLC (thin-layer chromatography), silica gel $GF_{254}$, developed in acetic acid:water:butanol=2:3:5, Rf=0.55]. The reaction mixture was diluted 10-fold with 10 mM, pH 5.2 acetate buffer, and loaded onto a DE 52 column (2×20 cm) The column was washed with starting buffer. Benzoyl AMP was eluted with 0–120 mM NaCl gradient (200 ml -200 ml). The preparation was lyophilized and subsequently desalted with P-2 BioGel chromatography in 1 mM HCl. Purified benzoyl AMP (76% separatory yield) gave m/z 452(M+H$^+$) by fast atom bombardment mass spectrometry (FAB-MS), and the following $^1$H-NMR properties (600 MHZ; $D_2O/DCl$): δ8.29 (1H, s), 8.09 (1H, s), 7.61 (2H, dd, J=8.2, 1.1), 7.47 (1H, t, J=7.5), 7.2 (2H, t, J=7.8), 6.01(1H, d, J=5.6), 4.9 (1H, t, J=5.5), 4.64(1H, dd, J=5.1, 4.2), 4.48–4.51 (2H, m), 4.39–4.43 (1H, m).

Spectroscopy

Mass spectra (MS) were obtained using a trio-1 MS linked with a 5890 Hewlett-Packard gas chromatograph. Electron impact (EI) ionization was performed at a high ionization voltage of 70 eV. GC separations were carried out on an OV-1 capillary column (10 m by 0.25 mm; 1 mm film thickness) with helium as carrier gas at a flow rate of 20 ml/min. The column oven temperature was held at 50° C. for 1 min, raised to 250° C. at a rate of 15° C./min, and held at that temperature for 10 min. Injector and detector temperatures were 220° and 270° C., respectively. The same MS was also equipped with a direct inlet probe. The probe temperature was set at 30° C. for 1 min, raised to 300° C. at 150° C./min, and held at 300° C. for 10 min for analysis. FAB mass analysis were performed using a ZAB-HF mass spectrometor (VG Analytical, Inc), at the mass spectrometry core facilities, department of Chemistry, University of Iowa. Ionizing matrices were either 3-nitrobenzyl alcohol or thioglycerol.

NMR spectra were obtained with a Bruker WM 360-MHZ high-field spectrometer equipped with an IBM Aspect-2000 processor. Tetramethylsilane was used as the internal standard for $^1H$ and $^{13}C$ spectra. Chemical shift values are reported in parts per million (ppm), and coupling constants (J values) are given in hertz. Abbreviations for NMR are as follows: s, singlet; d, doublet; t, triplet; dd, doublet of doublets; and m, multiplet. UV measurements were obtained with a Shimadzu UV-Visible Recording Spectrophotometer, model 160, in 1 cm quartz cuvettes.

In summary, the carboxylic acid reductase from Nocardia sp. NRRL 5646 is novel and unique In conclusion, the properties of the carboxylic acid reductase from Nocardia sp. NRRL 5646 clearly distinguish is from any enzyme or combination of enzymes in the prior art. The molecular weights of the present enzyme by SDS-PAGE and gel filtration chromatography were found to be in the same range as the results reported by Kato et al. for *Nocardia asteroides* JCM 3016 (*Agric. Biol Chem.* 55(3): 757 (1991)), and the mechanism of operation was found to be similar to the carboxylic acid reduction described by Gross and Zenk using Neurospora crassa (*Eur. J. Biochem.* 8:413 (1969)). However, the apparent Km values for benzoate, ATP and NADPH with the Nocardia sp NRRL 5646 carboxylic acid reductase enzyme were determined to be more than 1000-fold higher than those reported for preparations of *Nocardia asteroides*. The Km of benzoate for the crude Neurospora crassa reductase was reported to be 63 µM and its activity was inhibited by benzoate at 300 µM (id.). In contrast, no inhibition was observed for the present enzyme even when the benzoate concentration was as high as 2 mM, clearly demonstrating the novel and unique properties of the carboxylic acid reductase from Nocardia sp. NRRL 5646 as compared with the activities of crude whole-cell preparations reported by others in the prior art. Furthermore, this enzyme has a much broader substrate range than that of any other reported carboxylic acid reductase (see, Table 2).

Example 2

Biotransformation of Vanillic Acid to Vanillin by the Purified Carboxylic Acid Reductase for Nocardia sp NRRL 5646

The carboxylic acid reductase enzyme was purified from Nocardia sp. NRRL 5646 in accordance with the procedures set forth in Example 1, and used to demonstrate, for the first time, an enzymatic bio-conversion of vanillic acid to vanillin. The purity of the enzyme was established before each use by SDS-PAGE, as set forth in Example 1.

Enzymatic reduction was carried out in a reaction mixture of 200 ml 50 mM Tris-HCl buffer, containing 34 mg vanillic acid, 59 mg NADPH, 110 mg ATP, and 100 mg of purified carboxylic acid reductase (0.6 units). The reaction mixture was incubated at 30° C. with gentle shaking for 24 hours, after which the entire reaction mixture was loaded onto a solid phase extraction cartridge (Chem Elut 1200, 200 ml aqueous solution capacity). After 5 min. of equilibration, the cartridge was washed with 2×100 ml of hexane, then washed again with 2×100 ml of dichloromethane (concentrated to less than 2 ml).

The extract was then transferred to a vial and the solvent was removed with a stream of nitrogen to give about 8 mg of the purified vanillin end product.

TLC (silica gel developed in dichloromethane:ethylacetate:formic acid=95:5:1) analysis showed there was only one spot at Rf=0.42. It displayed orange color after being sprayed with 2,4-dinitrophenyl hydrazine. Mass spectrometry, $^1H$, and $^{13}C$ NMR data confirmed that this compound was vanillin. The yield was determined to be 96% with UV spectrophotometric assay at 340 nm.

This novel approach for the production of vanillin is attractive because the natural carboxylic acid starting materials are abundant, inexpensive, and soluble in aqueous media. The novel, purified enzyme system is particularly advantageous for reducing vanillic acid to vanillin, since the reduction of carboxylic acids to aldehydes has proven to be difficult to achieve by chemical means.

Example 3

An Elucidation of the Metabolic Pathways and Enzymes Involved in the Reduction of a Carboxylic Acid to its Corresponding Product(s) and By-Products by Nocardia sp. NRRL 5646

Using the Nocardia sp. NRRL 5646 cultures of Example 1, a 10% inoculum derived from a 72-hour first-stage culture was used to initiate the second-stage culture, which was incubated as before. After 24 h of incubation in the second stage, 2 ml of the selected carboxylic acid ("vanillic acid," also referred to as "compound 1a" from Aldrich Chemical Co.) (80 mg/ml in dimethyl sulfoxide) was added to each flask. Control cultures included everything except vanillic acid.

Substrates

In addition to the commercially available reagents, e.g., vanillic acid (4-hydroxy-3-methoxybenzoic acid; "compound 1a"), vanillin (4-hydroxy-3- methoxybenzaldehyde; "compound 3a"), vanillyl alcohol (4-hydroxy-3-methoxybenzyl alcohol; "compound 4a"), guaiacol (2-methoxyphenol; "compound 2"), and benzyl bromide, available from Aldrich Chemical Co., certain additional necessary reagents were prepared to evaluate the mechanisms and kinetics involved in the biotransformation of vanillic acid to its products and intermediary by-products. o-Benzylation of vanillic acid, of vanillin, and of vanillyl alcohol on their 4-hydroxy groups were carried out by following procedures.

An 11 ml aliquot of 1N NaOH was added to 16 ml of ethanol containing 900 mg vanillic acid. Benzyl bromide (1.0 g in 2.5 ml ethanol) was added to the vanillate solution dropwise over 60 min. The mixture was refluxed for 2 hours, until no vanillic acid could be detected by TLC using silica gel $GF_{254}$ (benzene:acetic acid=5:1.5). f values were as follows: benzyl alcohol, 0.42; vanillic acid, 0.47; o-benzyl vanillic acid, 0.62; and benzyl bromide, 0.78. The reaction mixture was poured into 150 ml water and acidified with 6N HCl to pH 2. The precipitate was collected by filtration and recrystallized in xylene to afford 802 mg product. The structure of the o-benzyl vanillic acid (compound 1b) was confirmed with following spectroscopic data: Low resolution EI mass spectrum, m/z 258 (8%, M$^+$), 91 (100%, benzonium ion); $^1H$ NMR 360 MHz ($d_6$-acetone) δH 3.83 [3H, s, OCH$_3$], 5.21 (2H, s, C-7'), 7.12, 7.14 (1H, d, J=8.3 Hz, H-5), 7.33–7.52 (5H, m, H-2', 3', 4', 5', 6'), 7.58, 7.57 (1H, d, J=2.0 Hz, H-2), 7.63–7.65 (1H, dd, J=8.3, 2.0 Hz, H-6); $^{13}C$ NMR ($d_6$-acetone) δC 56.2 (OCH$_3$), 71.1 (C-7'), 113.4 (C-5), 113.6 (C-2), 124.0 (C-1), 124.3 (C-6), 128.6 (C-3'), 128.8(C-4'), 129.3 (C-2') 137.9 C-1'), 150.3 (C-3), 153.3 (C-3), 167.4 (C-7).

To prepare o-benzyl vanillin (compound 3b), 30 g potassium bicarbonate was added to 200 ml of ethanol containing 32 g of vanillin, then 26 ml of benzyl bromide was added. The reaction mixture was refluxed for 5 hours, cooled to room temperature, and filtered to remove KBr salt. The filtrate was refrigerated at 4° C. overnight to allow for the crystallization of o-benzyl vanillin. Rf values on silica gel $GF_{254}$ (benzene:acetic acid=5:1.5) were: vanillin, 0.52; and o-benzyl vanillin, 0.71. The product was recrystallized in ethanol to afford 45.3 g product with the following spectroscopic data to confirm its structure: Low resolution EI mass spectrum, m/z 242 (4%, $M^+$), 91 (100%, benzonium ion); $^1H$ NMR 360 MHz ($CDCl_3$) δH 3.95 (3H, s, $OCH_3$), 5.25 (2H, s, C-7'), 7.00, 6.98 (1H, d, J=8.3 Hz, H-5), 7.34–7.43 (7H, m, H-2,6, 2', 3', 4', 5', 6'), 9.84 (1H, s, H-7), $^{13}C$ NMR ($CDCl_3$) dC 56.0 ($OCH_3$), 70.8 (C-7'), 109.2 (C-2'), 112.3 (C-5), 126.5 (C-2), 127.1 (C-4'), 128.1 (C-6), 128.6 (C-3'), 130.2 (C-1), 135.9 (C-3), 149.9 (C-4), 159.9 (C-1'), 190.8 (C-7).

To prepare o-benzyl vanillyl alcohol (compound 4b), 15 g potassium bicarbonate was added to 80 ml of ethanol containing 16 g of vanillyl alcohol. To this mixture, 35 ml ethanol solution of benzyl bromide (0.5 g/ml) was added dropwise over 30 min. The reactants were refluxed for 3 h until vanillyl alcohol disappeared on TLC. The reaction mixture was then poured in 900 ml water to precipitate the product. The precipitate was dried under vacuum. The pure product was obtained by recrystallization in cyclohexane in 64% yield. Rf values are (silica gel $GF_{254}$, dichloromethane:acetic acid:benzene=100:6:4): vanillyl alcohol 0.10, o-benzyl vanillyl alcohol 0.31, benzyl bromide 0.79. The spectroscopy data were collected to confirm the structure: Low resolution FAB mass spectrum, as determined by the methods described in Example 1, m/z 244 (17%, M+), 227 (9%, M+—OH), 91 (100%, benzonium ion); $^1H$ NMR 360 MHz ($CDCl_3$) δH 3.89 (3H, s, $OCH_3$), 4.58 (2H, s, C-7), 5.16 (2H, s, H-7'), 6.76–6.79 (1H, dd, J=8.3, 1.9 Hz, H-6), 6.82, 6.84 (1H, d, J=8.2 Hz, H-5), 6.91, 6.92 (1H, d, J=1.7 Hz, H-2), 7.26–7.43 (5H, m, H-2', 3', 4', 5', 6'); $^{13}C$ NMR ($CDCl_3$) δC 55.9 ($OCH_3$), 65.0 (C-7), 71.0 (C-7'), 110.9 (C-2), 113.9 (C-5), 119.2 (C-4'), 127.1 (C-6), 127.7 (C-2'), 128.4 (C-3'), 134.1 (C-1), 137.0 (C-1'), 147.5 (C-3), 149.6 (C-4).

Chromatography methods

Thin layer chromatography (TLC) was carried out throughout the vanillic acid biotransformation on silica gel 60 F254 plates (E. Merck, Darmstadt, Germany). The developing solvent was a mixture of dichloromethane:acetonitrile:formic acid (75:25:1 vol/vol/vol). Developed chromatograms were directly visualized under 254-nm UV light to observe florescence quenching. Phenolic compounds were also visualized with Pauly's reagent, which consisted of solution A (0.5% sulfanilic acid in 2N HCl), solution B (0.5% sodium nitrite in water), and solution C (1N potassium hydroxide in 50% ethanol-water). Developed plates were first sprayed with a freshly prepared equal-volume mixture of A and B, and then were sprayed with solution C before being heated with a heat gun to develop colors from yellow to orange. Aldehydes such as vanillin were also detected with 2,4,-dinitrophenylhydrazine (0.4% in 2N HCl, wt/vol) spray. The Rf values for vanillic acid, vanillin, vanillyl alcohol, and guaiacol were determined to be 0.46, 0.35, 0.77, and 0.89, respectively.

For preparative thin layer chromatography in vanillic acid transformation, the dichloromethane extracts were streaked onto a 1 mm thick preparative TLC plate (20×20 cm), which was developed in the same solvent. The separated bands after development were scraped from the plate and the compounds were eluted from silica gel with a mixture of dichloromethane and acetonitrile (70:30, vol/vol). The band extracts were checked for purity by TLC, and concentrated for spectral analysis.

Over the course of vanillic acid transformation, 3 ml culture samples were taken. To each sample, 200 µl of o-anisic acid solution (30 mg/ml in acetonitrile) was added as an internal standard. The culture was acidified to pH 2 with 6N HCl, and a sample (1 ml of the acidified culture) was loaded onto a solid phase extraction cartridge (Chem Elut CE 1001, 1 ml aqueous solution capacity, Varian, Harbor City, Cailf.). After 5 min, the cartridge was extracted with 3 ml of dichloromethane:acetonitrile (90:10); twice for subsequent HPLC quantification.

HPLC was performed with a Shimadzu liquid chromatograph equipped with four pumps (FCV-10AL), a photodiode array UV-V is detector (SPD-M6A), and a system controller (LC-10AD). Separations were carried out under isocratic conditions over a Versapack C18 column (250 by 4.6 mm, 10 mm particle size; Alltech, Deerfield, Ill.) with a mobile phase including acetonitrile:water:formic acid (20:80:1) at a flow rate of 0.9 ml/min. The eluted peaks were detected at 273–276 nm and were identified by HPLC comparison with authentic compounds (see, FIG. 5). HPLC retention volumes (Rv) were 5.0 ml for vanillyl alcohol, 8.1 ml for vanillic acid, 13.2 ml for vanillin, 16.1 ml for o-anisic acid, and 18.7 ml for guaiacol. Standard curves for vanillic acid (compound 1a), vanillin (compound 3a), vanillyl alcohol (compound 4a), and guaiacol (compound 2) were established over the range of 0.3 mg to 8 mg. Typically, 10–30 µl of samples were injected to maintain peaks within detection range. The concentration of each metabolite was determined by comparing relative peak area ratios to that of the internal standard.

In o-benzyl vanillic acid (compound 1b) biotransformation, TLC was carried out on silica gel $GF_{254}$ plates. The developing solvents was a mixture of dichloromethane:acetic acid:benzene (100:2:2, vol/vol/vol). Developed chromatograms were visualized under 254 nm UV light. The Rf values for o-benzyl vanillic acid (compound 1b), o-benzyl vanillin (compound 3b), and o-benzyl vanillyl alcohol (compound 4b) are 0.70, 0.83, and 0.19, respectively. For preparative chromatography, concentrated ethyl acetate extracts were reconstituted to 2.0 ml with dichloromethane and loaded onto a 0.9×20 cm silica gel column. o-Benzyl vanillin was eluted with dichloromethane. o-Benzyl vanillic acid was separated from o-benzyl vanillyl alcohol with a mixture of dichloromethane, benzene, and acetic acid (100:4:6, vol/vol/vol).

To quantify the o-benzyl vanillic acid transformation, 50 µl of p-anisic acid (4 mg/ml in methanol) was added to 1 ml sample as an internal standard. Samples were acidified to pH 2 with 6N HCl and loaded onto solid phase extraction cartridges (Chem Elut CE 1001, 1 ml aqueous solution capacity), which were eluted twice with 3 ml ethyl acetate after 5 min equilibration. Pooled eluates were subjected to HPLC analysis, and HPLC was performed with a Shimadzu liquid chromatograph equipped with a SCL 6-B system controller, two LC-6A pumps and a variable-wave-length UV detector set at 290 nm. The separation was carried out under isocratic conditions over a 10 m C18 Versapack column (300 by 4.1 mm, Alltech) with a mobile phase of $CH_3CN$:water:formic acid (30:70:1) at a flow rate of 2 ml/min. Retention volumes (Rv) were 8.1 ml for p-anisic acid, 21.9 ml for o-benzyl vanillyl alcohol (compound 4b), 33.4 ml for o-benzyl vanillic acid (compound 1b), and 61.1 ml for o-benzyl vanillin (compound 3b).

Standard curves for each compound was established over a range of from 0.3 µg to 3 µg. Typically, 10–50 µl of samples were injected to maintain the peaks within detection range. The concentration of each metabolite was determined by peak area ratios to that of the internal standard.

Transformation of vanillic acid (compound 1a) in the presence of growing cells of Nocardia sp.

Shaken flask cultures were grown by a standard two stage incubation protocol of Example 1 in 200 ml of sterile soybean flour-glucose medium held in stainless steel-capped 1-liter DeLong culture flasks. A 10% inoculum derived from a 72-hour first-stage culture was used to initiate the second-stage culture, which was incubated as before. After 24 hours of incubation in the second stage, 2 ml of vanillic acid (80 mg/ml in dimethyl sulfoxide) was added to each flask as in Example 2. Control cultures were identical, exclusive of the addition of vanillic acid.

Vanillic acid containing cultures were generally sampled by removing 1 ml of the entire culture. Samples were adjusted to pH 2 with 6N HCl and extracted with an equal volume of ethyl acetate. The organic solvent was separated from the aqueous media by centrifugation for 1 min. at 2,500 rpm in a desktop centrifuge. The organic solvent layer was removed, evaporated to dryness, and reconstituted in 0.5 ml methanol. Then the samples were spotted onto TLC plates for analysis.

For preparative biotransformation, the microbial reaction was terminated at 40 hours after addition of the vanillic acid. The culture was acidified to pH 2 with 6N HCl, a total of 200 ml of the acidified culture was loaded onto a solid phase extraction cartridge (Chem Elut 1200, 200 ml aqueous solution capacity). After 5 min of equilibration, the cartridge was washed three times with 200 ml hexane each time, then rewashed three times with 200 ml dichloromethane each time. The organic extracts were concentrated by rotary evaporation to give 45 mg oil (from hexane) and 90 mg of residue (from dichloromethane).

The hexane extract from the 40 h transformation culture gave 45 mg oil like substance. TLC analysis showed that it gave a single spot at $Rf=0.89$, which turned orange after Pauly's reagent spray. Spectroscopy analysis, as described in Example 1, allowed us to identify this compound as guaiacol (compound 2) with the following data: Low-resolution EI mass spectrum, m/z (percent relative abundance) 124 (78%, M+), 109 (92%, M+—$CH_3$), 91 (44%, M+—$CH_3$—$H_2O$), and 81(100%, $M^+$—$CH_3$—CO); $^1$H NMR 360 MHz ($CDCl_3$) δH, 3.76 (3H, s, $OCH_3$), 6.80–6.85 (3H, m, H-3, H-4, H-6), 6.90–6.93 (1H, m, H-5); $^{13}$C NMR ($CDCl_3$) bδH, 3.76 (3H, s, $OCH_3$), 110.9 (C-5), 114.7 (C-4), 120.2 (C-6), 121.5 (C-3), 145.7 (C-1), 146.7 (C-2).

The dichloromethane extract was further purified with silica gel chromatography, and two compounds were isolated (about 4 mg each). One of the compounds was found to have an $Rf=0.77$ and the spectroscopy data were in good agreement with vanillin (compound 3a): Low-resolution EI mass spectrum, m/z 152 (88%, $M^+$), 151(100%, $M^{30}$—H), 137(6%, $M^+$—$CH_3$), 123 (13%, $M^+$—CHO); $^1$H NMR 360 MHz ($CDCl_3$)δH, 3.96 (3H, OCH3), 6.22 (1H, s, OH), 7.03–7.06 (1H, m, H-5), 7.26–7.44 (2H, m, H-2, H-6), 9.83 (1H, s, CHO); $^{13}$C NMR ($CDCl_3$) δC 56.1 ($OCH_3$), 108.7 (C-6), 114.3 (C-2), 127.5 (C-5), 129.8 (C-1), 147.1 (C-4), 151.6 (C-3), 190.8 (C-7).

The second compound was found to have an $Rf=0.35$ and the spectroscopy data were in good agreement with vanillyl alcohol (compound 4a): Low-resolution EI mass spectrum, m/z 154 (28%, $M^+$), 136 (50%, $M^+$—$H_2O$); $^1$H NMR 360 MHz ($CDCl_3$) δH 3.90 (3H, s, $OCH_3$), 4.61(2H, s, $CH_2OH$), 6.82–6.92 (3H, m, H-2, H-5, H-6); $^{13}$C NMR ($CDCl_3$) δC 55.9 ($OCH_3$), 66.5 (C-7), 110.0 (C-2), 114.3 (C-5), 120.3 (C-6), 132.9 (C-1), 145.3 (C-4), 146.7 (C-3).

Thus the metabolite identification led to the conclusion that there are two metabolism pathways for vanillic acid transformation by Nocardia sp. NRRL 5646 (FIG. 7): one is the reduction to vanillin and further to vanillyl alcohol; the other is decarboxylation to guaiacol.

Figure 6:
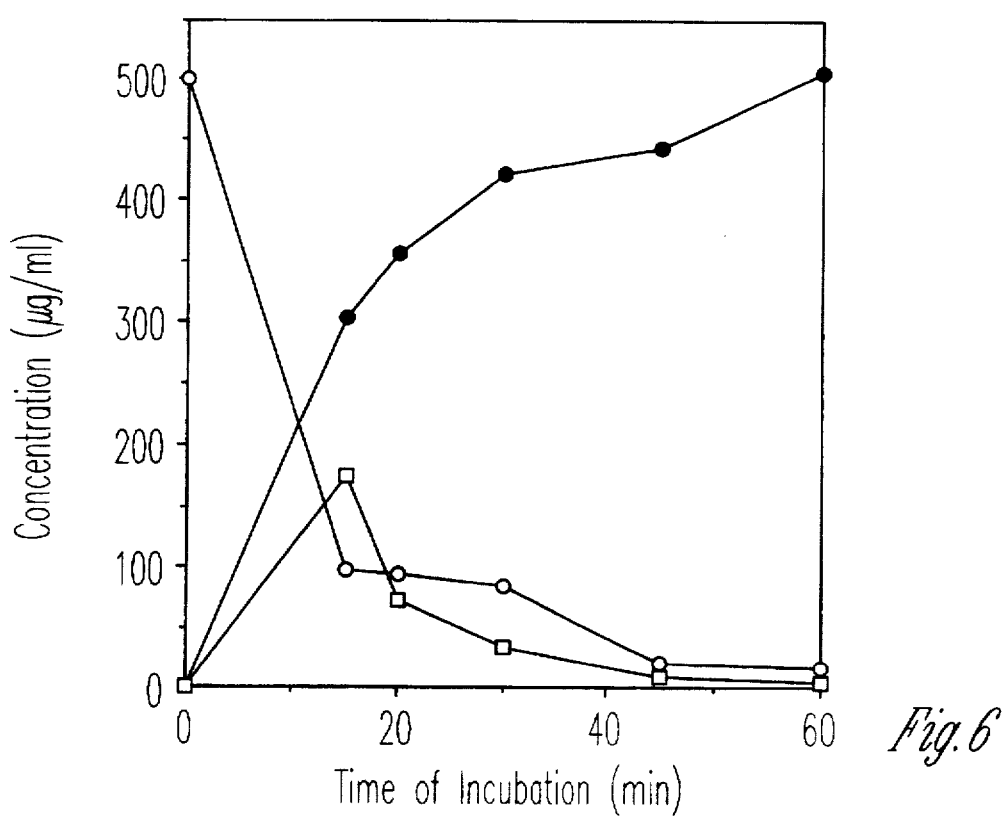
FIG. 6 depicts the time course of resting cell transformation of o-benzyl vanillic acid by Nocardia sp NRRL 646. Each data point represents the average of three repeats: open circles (○), o-benzyl vanillic acid; open squares (□), o-benzyl vanillin; closed circles (●), o-benzyl vanillyl alcohol.
Figure 1:
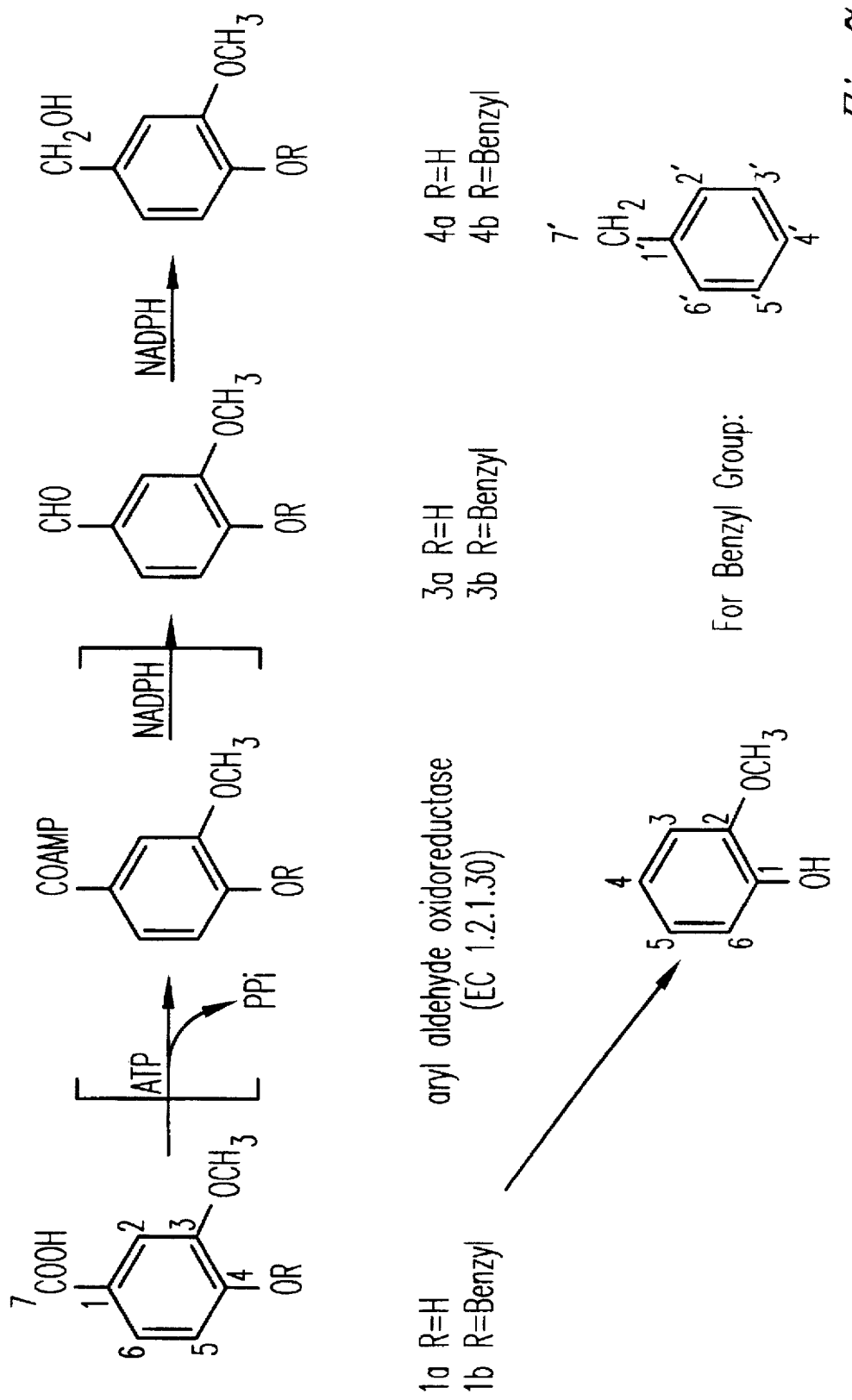

The rates to transform vanillic acid in the two metabolic pathways were determined with HPLC quantification (FIG. 6), wherein it was shown that almost all of the vanillic acid was metabolized in 48 hours in the presence of the growing culture (69% of the substrate was decarboxylated to give guaiacol, and 11% of the substrate were reduced to vanillyl alcohol as the final product). Although the eluted peaks were also monitored at 254 nm, no other aromatic metabolites were detected.

Transformation of o-benzylated vanillic acid (compound 1b) in the presence of resting cells of Nocardia sp As above, Nocardia sp. was grown using the standard two stage incubation protocol. After 24 hours, 5 mg/ml benzoic acid was added to the second stage culture as an inducer for the synthesis of the carboxylic acid reductase (aryl aldehyde oxidoreductase) synthesis (Li and Rosazza, J. Bacteriol. (1997; submitted)). As in Example 1, the culture was harvested 24 hours after addition of benzoate, the cells were collected by centrifugation at 8,000×g for 20 min, and washed twice with 0.9% NaCl.

For preparative biotransformations, 2.8 g wet cells were suspended in 400 ml of 50 mM Tris HCl, pH 7.4 containing 1% glucose, 10 mM $MgCl_2$, and 5 mM phosphate. o-Benzyl vanillic acid (0.7 g in 2 ml dimethylsulfoxide) was added to the cell suspension, which was incubated by shaking at 150 rpm at 30° C. for 15 min. The reaction mixture was acidified and subsequently loaded onto two solid phase extraction cartridges (Chem Elut 1200, 200 ml each). After 5 min equilibration, each cartridge was washed with 3×200 ml ethyl acetate. The ethyl acetate solution was concentrated by rotary evaporation to yield 670 mg of crude product.

For HPLC quantification, the transformation medium was the same as that for preparative biotransformations. A cell suspension of 0.05 g/ml (wet weight) containing 0.6 mg/ml o-benzylated vanillic acid was incubated at 30° C. During the course of incubation, samples of 1 ml reaction medium were taken and analyzed as described (see, FIG. 7). For comparison purposes, pure vanillin was chemically produced by the de-benzylation of o-benzyl vanillin ("compound 3b"). One (1.0) ml o-benzyl vanillin (170 mg/ml in ethanol) was added to a mixture of 5 ml concentrated HCl and 2 ml ethanol. The reaction mixture was refluxed for 2 hours, after which the solvent was removed by rotary evaporation, and 0.5 ml dichloromethane was added to reconstitute. Vanillin (compound 3a) was purified by silica gel column chromatography (0.9×5 cm) eluted with dichloromethane.

TLC analysis identified two products with Rf values of 0.83, and 0.19, corresponding to o-benzyl vanillin (compound 3b) and o-benzyl vanillyl alcohol (compound 4b), respectively. The metabolite at $Rf=0.83$ on TLC could also be detected with 2,4-dinitrophenyl-hydrazine spray.

Figure 5:
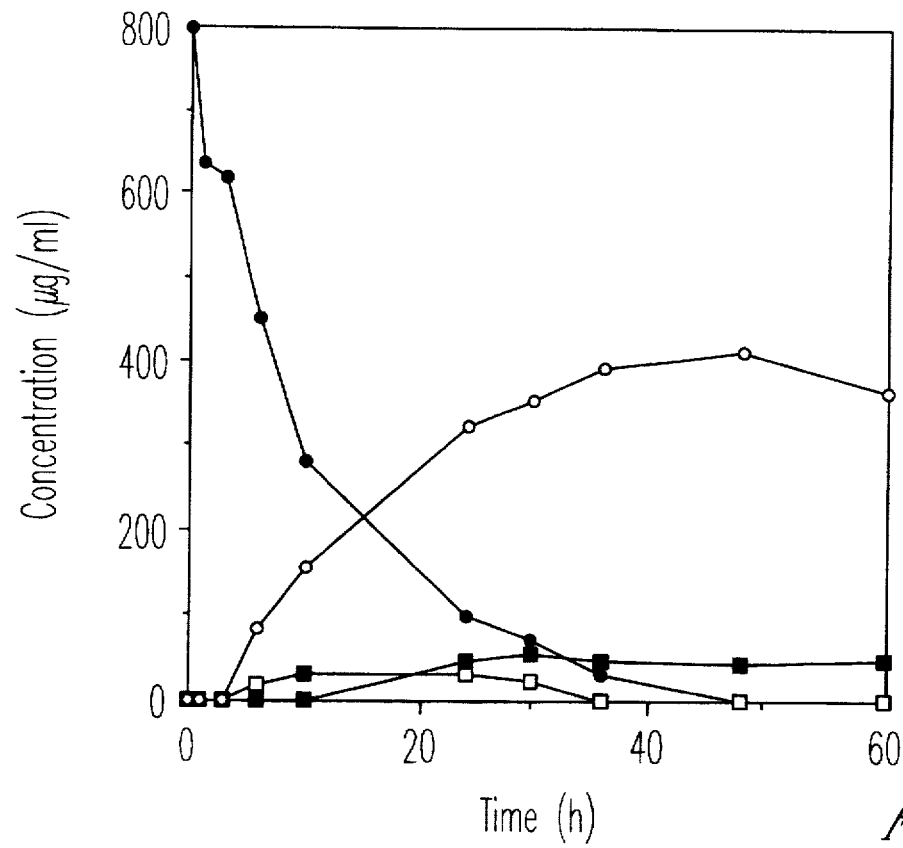
FIG. 5 depicts the time course of growing cell transformation of vanillic acid by Nocardia sp. NRRL 5646. Each data point represents the average of three repeats: closed circles (●), vanillic acid; closed squares (■), vanillyl alcohol; open squares (□), vanillin; open circles (○), guaiacol.

Samples of 0.17 g of the compound with $Rf=0.83$, and 0.21 g of the compound with $Rf=0.19$ were purified from the ethyl acetate extract of the preparative biotransformation culture, and mass spectrometry, as described in Example 1. $^1$H, and $^{13}$C NMR data were obtained for each. Comparison with the data for the synthetic compounds, identified the compound with $Rf=0.83$ as o-benzyl vanillin (compound 3b), and the other compound as o-benzyl vanillyl alcohol (compound 4b). Thus is was apparent that the pathway for the transformation of o-benzyl vanillic acid was first the reduction of carboxylic acid to aldehyde, and subsequently dehydrogenation to alcohol as shown in FIG. 5.

Debenzylation of compound 3b, followed by silica gel chromatography, yielded 65 mg aldehyde. Mass spectrometry, $^1$H, and $^{13}$C NMR data identified the aldehyde to be vanillin (compound 3a) by comparison with representative data for plant-derived vanillin.

HPLC quantification (FIG. 7) of the biotransformation showed that in 60 min. the benzylated vanillin could be transformed almost quantitatively into the corresponding alcohol final product. In the course of producing the alcohol, there was a transient accumulation of aldehyde at a concentration of up to 175 µg/ml within 15 min.

Example 4

The Reduction of Benzoyl-AMP to Benzaldehyde Catalyzed by Purified Carboxylic Acid Reductase from Nocardia sp. NRRL 5646

Using carboxyl-$^{13}$C labeled benzoyl-AMP, synthesized as described in Example 1, the reduction of benzoyl-AMP to benzaldehyde with the substantially purified carboxylic acid reductase from Nocardia sp. NRRL 5646 was investigated with $^{13}$C NMR spectroscopy (see, FIG. 1). The substantially purified carboxylic acid reductase from Nocardia sp. NRRL 5646 and all other reagents were prepared or obtained in Example 1.

The reaction mixture included: 1.4 mM carboxyl-$^{13}$C labeled benzoyl-AMP, and 2.0 mM NADPH in 0.5 ml 50 mM Tris-HCl, pH 7.5. A 10 µl sample (0.05 units) of the substantially purified carboxylic acid reductase was added to initiate the reaction. A control sample was prepared containing everything except the enzyme. After 20 min. incubation at 20° C., the samples were subjected to NMR analysis. For $^{13}$C NMR spectroscopy, 20 ml D$_2$O was added as the locking solvent, and 5 ml of dioxane was added as an internal standard (67.4 ppm). NMR spectra were obtained with a Bruker WM 360-MHZ high-field spectrometer equipped with an IBM Aspect-2000 processor.

Figure 8B:
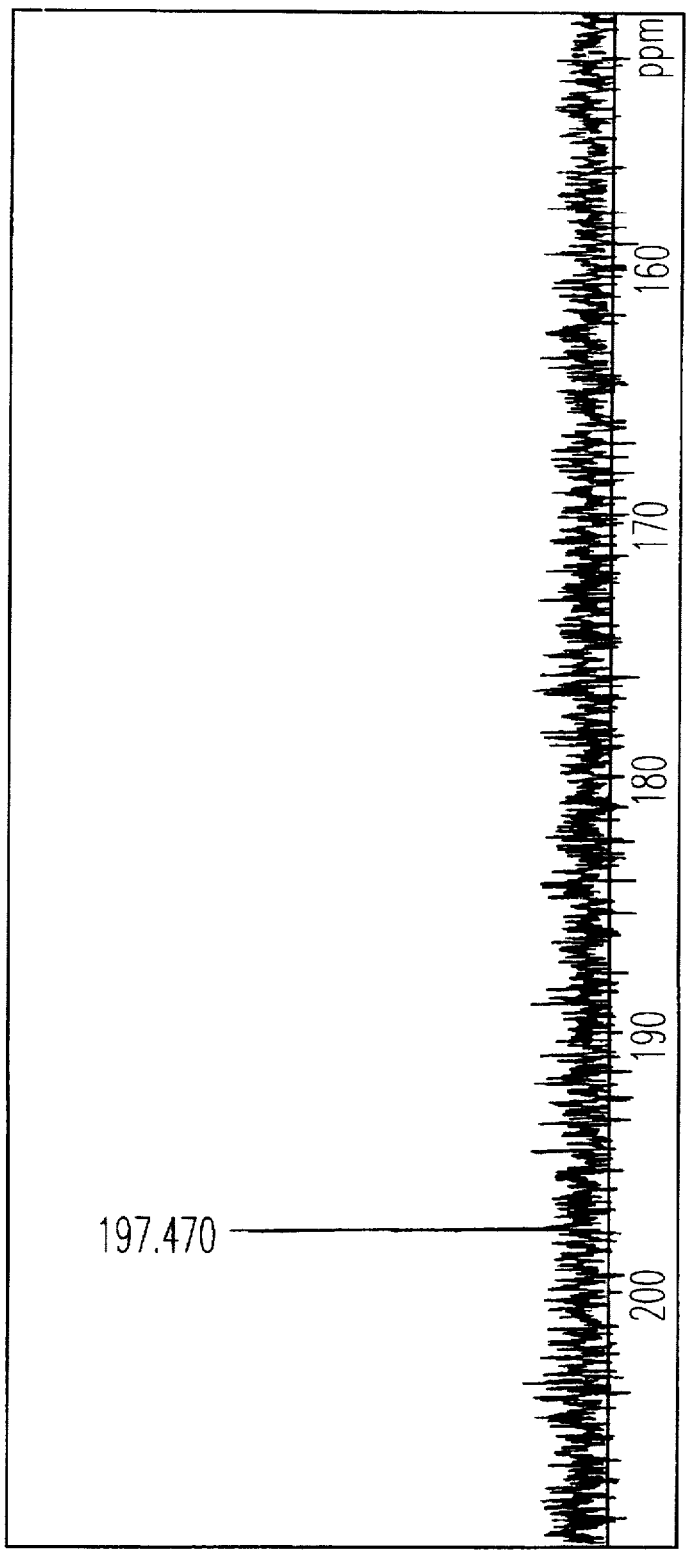
FIG. 8 depicts the $^{13}C$ NMR study of benzoyl-AMP reduction catalyzed by the substantially purified carboxylic acid reductase obtained from Nocardia sp NRRL 5646. Panel A: control sample. Panel B: enzyme catalyzed reduction sample.

As seen in FIG. 8A, the $^{13}$C spectrum for the control sample displayed a small singlet at 176.2 ppm, which corresponds to the carboxy carbon in benzoic acid, and a doublet at 164.8 ppm, which corresponds to the carboxy carbon in benzoyl-AMP. By comparison, the $^{13}$C spectrum for the enzyme catalyzed reduction displayed only one peak at 197.5 ppm as seen in FIG. 8B, which corresponds to the aldehyde carbon signal. The absence of any other signal in the reduced sample indicates that all of the benzoyl-AMP was completely reduced to benzaldehyde.

This result proves that an intermediate, benzoyl-AMP, normally produced during the enzymatic reduction of benzoic acid into its aldehyde product, can be quantitatively reduced in the presence of NADPH, to benzaldehyde. This further establishes that the reduction pathway of a carboxylic acid to its aldehyde product is as shown in FIG. 1 when the biocatalytic enzyme is the substantially purified carboxylic acid reductase from Nocardia sp. NRRL 5646.

Although the present invention has been described with reference to the presently preferred embodiments and examples, the skilled artisan will appreciate that various modifications, substitutions, omissions and changes may be made without departing from the spirit of the invention.

---

What is claimed is:

1. A substantially purified, biologically-derived carboxylic acid reductase, isolated from Nocardia sp. strain NRRL 5646 having the N-terminal amino acid sequence of SEQ ID NO:1, wherein the enzyme is characterized by its ability to biocatalytically reduce a carboxylic acid, or a derivative thereof, to its corresponding product(s) and intermediary by-product(s), and further characterized by its ability to reduce vanillic acid to vanillin.

2. An enzyme according to claim 1 further characterized as having an absorption maxima at 214 and 283 nm by UV visible spectroscopy.

3. An enzyme according to claim 1 further characterized as having a native molecular weight of 163.3±4.8 kDa (n=3).

4. An enzyme according to claim 1 further characterized as not being inhibited by benzoate concentrations of at least 2 mM.

5. An enzyme according to claim 1 characterized by having the internal amino acid sequence of SEQUENCE ID NO:2.

* * * * *